US006270769B1

(12) United States Patent
Raychaudhuri et al.

(10) Patent No.: US 6,270,769 B1
(45) Date of Patent: *Aug. 7, 2001

(54) INDUCTION OF CYTOTOXIC T-LYMPHOCYTE RESPONSES

(75) Inventors: Syamal Raychaudhuri, San Diego; William H. Rastetter, Rancho Santa Fe, both of CA (US)

(73) Assignee: IDEC Pharmaceuticals Corporation, San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/449,728

(22) Filed: May 24, 1995

Related U.S. Application Data

(63) Continuation of application No. 07/919,787, filed on Jul. 24, 1992, now Pat. No. 5,585,103, which is a continuation-in-part of application No. 07/735,069, filed on Jul. 25, 1991, now abandoned.

(51) Int. Cl.[7] ............... A61K 39/000; A61K 39/002; A61K 39/12; A61K 39/39
(52) U.S. Cl. .................. 424/184.1; 424/204.1; 424/208.1; 424/278.1; 424/283.1; 424/400
(58) Field of Search ............... 424/208.1, 184.1, 424/278.1, 283.1, 204.1, 400

(56) References Cited

U.S. PATENT DOCUMENTS 4,770,874 * 9/1988 Allison .................. 424/88

FOREIGN PATENT DOCUMENTS

0451216 B1 * 10/1991 (EP).
0682040 A1 * 11/1995 (EP).

OTHER PUBLICATIONS

Mackewicz et al. 1991 J. Clin. Invest. 87:1462–66.*
Brugh et al. 1983 Am J Vet Res 44(1)72–75.*
Byars et al. 1987 Vaccine 5, pp. 223–228.*
Acres et al. J. Immunotherapy 1993 14(2)136–43.*
Nicholas et al. 1991 Virology 182(2)664–72.*
Alwan et al. 1992 Clin Exp Immurol 88(3) 527–36.*
Peace et al. 1993 J. Immunother. 14(2)110–14.*
Yin et al. 1993 Leukemia 7 Suppl 2 527–30.*

* cited by examiner

Primary Examiner—Michael P. Woodward
Assistant Examiner—Mary K Zeman
(74) Attorney, Agent, or Firm—Burns, Doane, Swecker & Mathis

(57) ABSTRACT

Methods and compositions useful for inducing a cytotoxic T lymphocyte response (CTL) in a human or domesticated or agriculturally important animal. The method includes the steps of providing the antigen to which the CTL response is desired and providing an antigen formulation which comprises, consists, or consists essentially of two or more of a stabilizing detergent, a micelle-forming agent, and an oil. This antigen formulation is preferably lacking in an immunostimulating peptide component, or has sufficiently low levels of such a component that the desired CTL response is not diminished. This formulation is provided as a stable oil-in-water emulsion.

35 Claims, 12 Drawing Sheets

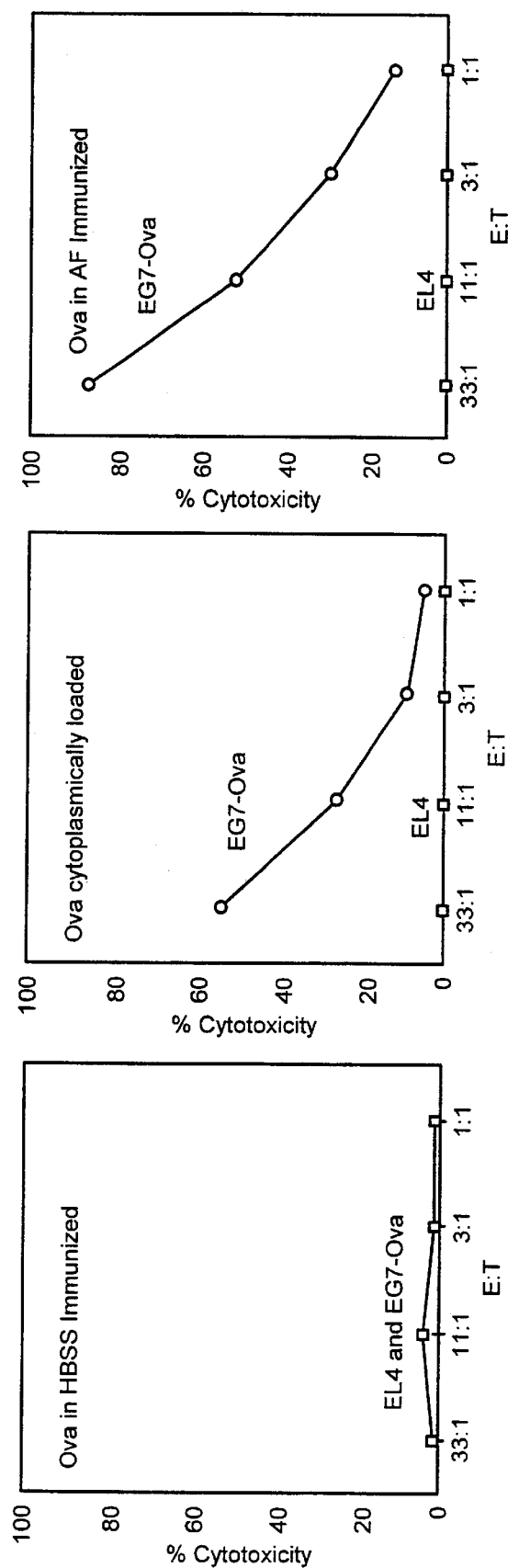

SEQUENCE LISTING (1) GENERAL INFORMATION:

(iii) NUMBER OF SEQUENCES:   2

(2) INFORMATION FOR SEQ ID NO:   1:

(i) SEQUENCE CHARACTERISTICS:
      (A) LENGTH:     24
      (B) TYPE:       amino acid
      (C) STRANDEDNESS: single
      (D) TOPOLOGY:   linear (ii) SEQUENCE DESCRIPTION: SEQ ID NO: 1:

Glu Gln Leu Glu Ser Ile Ile Asn Phe Glu Lys Leu Thr Glu Trp Thr
1             5                  10               15

Ser Ser Asn Val Met Glu Glu Arg
            20

(2) INFORMATION FOR SEQ ID NO:   2:

(i) SEQUENCE CHARACTERISTICS:
      (A) LENGTH:     19
      (B) TYPE:       amino acid
      (C) STRANDEDNESS: single
      (D) TOPOLOGY:   linear (ii) SEQUENCE DESCRIPTION: SEQ ID NO: 2:

Asp Glu Asn Pro Val Val His Phe Phe Lys Asn Ile Val Thr Pro Arg
1             5                  10               15

Thr Pro Pro

INDUCTION OF CYTOTOXIC T-LYMPHOCYTE RESPONSES

This application is a continuation of application Ser. No. 07/919,787, U.S. Pat. No. 5,585,103 filed Jul. 24, 1992, which is a continuation-in-part of U.S. application Ser. No. 07/735,069, filed Jul. 25, 1991 (now abandoned).

BACKGROUND OF THE INVENTION

This is a continuation-in-part of U.S. Ser. No. 07/735,069, filed Jul. 25, 1991, entitled "Induction of Cytotoxic T-Lymphocyte Responses," by Syamal Raychaudhuri and William H. Rastetter. This invention relates to methods and compositions useful for inducing cytotoxic T-cell mediated responses in humans, and domesticated or agricultural animals.

Cytotoxic T-lymphocytes (CTLs) are believed to be the major host defense mechanism in response to a variety of viral infections and neoplastic or cancerous growth. These cells eliminate infected or transformed cells by recognizing antigen fragments in association with various molecules (termed class I MHC molecules) on the infected or transformed cells. CTLs may be induced experimentally by cytoplasmic loading of certain soluble antigens within specific cells. Immunization with the soluble antigen alone is generally insufficient for specific cytotoxic T-lymphocyte induction.

One method by which CTL response may be induced involves the use of recombinant engineering techniques to incorporate critical components of an antigen in question into the genome of a benign infectious agent. The aim of such a strategy is to generate antigen-specific cytotoxic T-lymphocyte responses to the desired epitope by subjecting the host to a mild, self-limiting infection. Chimeric vectors have been described using vaccinia, polio, adeno- and retro-viruses, as well as bacteria such as Listeria and BCG. For example, Takahashi et al. 85 *Proc. Natl. Acad. Sci., USA* 3105, 1988 describe use of recombinant vaccinia virus expressing the HIV gp160 envelope gene as a potential tool for induction of cytotoxic T-lymphocytes.

A second method by which a cell mediated response may be induced involves the use of adjuvants. While the art appears replete with discussion of the use of adjuvants, it is unclear in such art whether cell mediated immunity was induced and whether such cell mediated immunity included a cytotoxic T-lymphocyte response. The following, however, are representative of various publications in this area.

Stover et al., 351 *Nature* 456, 1991 (not admitted to be prior art to the present application) describes a CTL response to β-galactosidase using recombinant BCG containing a β-galactosidase gene. No such response was detected using incomplete Freund's adjuvant and β-galactosidase.

Mitchell et al., 8 *J. Clinical Oncology* 856, 1990 (which is not admitted to be prior art to the present invention) describe treatment of metatastic melanoma patients with an adjuvant termed "DETOX" and allogeneic melanoma lysates administered five times over a period of six weeks. In a small portion of the patients an increase in cytolytic T-cells was observed. The authors describe a need to enhance the level of cytotoxic T-lymphocyte production, and suggest a combined therapy of adjuvant with Interleukin-2, as well as a pretreatment with cyclophosphamide to diminish the level of tumor specific T-suppressor cells that might exist. DETOX includes detoxified endotoxin (monophosphoryl lipid A) from *Salmonella minnesota*, cell wall skeletons of *Mycobacterium phlei*, squalene oil and emulsifier.

Allison and Gregoriadis, 11 *Immunology Today* 427, 1990 (which is not admitted to be prior art to the present invention) note that the only adjuvant "authorized for use" in human vaccines is aluminum salts (alum) which does not consistently elicit cell mediated immunity. Allison and Gregoriadis state "[t]here is, therefore, a need to develop adjuvants with the efficacy of Freund's complete adjuvant but without its various side effects such as granulomas." They go on to state that three possible strategies exist, for example, the use of liposomes; the use of adjuvants, termed immunostimulating complexes (ISCOMs, which include saponin or Quil A (a triterpenoid with two carbohydrate chains), cholesterol, and phosphatidyl choline) which are authorized for use in an influenza vaccine for horses (Morein et al., *Immunological Adjuvants and Vaccines*, Plenum Press, 153); and the use of an emulsion (SAF) of squalene or squalane (with or without a pluronic agent) and muramyl dipeptide (MDP). SAF is said to elicit a cell mediated immunity in mice, although it "has long been thought that subunit antigens cannot elicit cytotoxic T-cell (CTL) responses."

Takahashi et al., 344 *Nature* 873, 1990, describe class II restricted helper and cytotoxic T-lymphocyte induction by use of ISCOMs with a single subcutaneous immunization in mice. They state that Freund's adjuvant, incomplete Freund's adjuvant, and phosphate buffered saline did not induce cytotoxic T-lymphocyte activity against the targets in which they were interested. They state that, in contrast to results with other forms of exogenous soluble protein antigen, they have shown that it is possible to prime antigen specific MHC class I restricted $CD8^+$ $CD4^-$ CTL by immunization with exogenous intact protein using ISCOMs. They also state that the experiments described suggest that it may be possible to elicit human CTL by using ISCOMs containing HIV proteins, and that ISCOM-based vaccines may achieve the long sought goal of induction of both CTL and antibodies by a purified protein.

Byars and Allison, 5 Vaccines 223, 1987 describe use of SAF-1 which includes TWEEN 80, PLURONIC L121, and squalene or squalane, with or without muramyl dipeptide, and suggest that their data indicate that the formulation with muramyl dipeptide will be useful for human and veterinary vaccines. Booster shots of the adjuvant were provided without the muramyl dipeptide. The muramyl dipeptide is said to increase antibody production significantly over use of the adjuvant without muramyl dipeptide. Cell mediated immunity was measured as delayed type hypersensitivity by skin tests to determine T-helper cell induction. Such hypersensitivity was stronger and more sustained when muramyl dipeptide was provided in the adjuvant. Similar adjuvants are described by Allison et al., U.S. Pat. No. 4,770,874 (where it is stated that the combination of muramyl dipeptide and pluronic polyol is essential to elicit a powerful cell mediated and humoral response against egg albumin); Allison et al., U.S. Pat. No. 4,772,466; Murphy-Corb et al., 246 *Science* 1293, 1989 (where it is stated that the use of combined adjuvants with muramyl dipeptide might enhance induction of both humoral and cellular arms of the immune response); Allison and Byars, 87 *Vaccines* 56, 1987 (where it is stated that cell mediated immunity is elicited by SAF (with muramyl dipeptide) as shown by delayed type hypersensitivity, by proliferative responses of T-cells to antigen, by production of Interleukin-2, and by specific genetically restricted lysis of target cells bearing the immunizing antigen); Allison and Byars, *Immunopharmacology of Infectious Diseases: Vaccine Adjuvants and Modulators of Non-Specific Resistance* 191–201, 1987; Morgan et al., 29 *J. Medical Virology* 74, 1989; Kenney et al., 121 *J. Immunological Methods* 157, 1989; Allison and Byars, 95 *J. Immunological Methods* 157, 1986 (where aluminum salts and mineral oil emulsions were shown to increase antibody formation, but not cell mediated immunity; and muramyl dipeptide formulations were shown to elicit cell mediated immunity); Byars et al., 8 *Vaccine* 49, 1990 (not admitted to be prior art to the present application, where it is stated that their adjuvant formulation markedly increases humoral responses, and to a lesser degree enhances cell mediated reactions to influenzae haemagglutinin antigen); Allison and Byars, 28 *Molecular Immunology* 279, 1991 (not admitted to be prior art to the present application; which states that the function of the muramyl dipeptide is to induce expression of cytokines and increase expression of major histocompatibility (MHC) genes; and that better antibody and cellular responses were obtained than with other adjuvants, and that it is hoped to ascertain whether similar strategies are efficacious in humans); Allison and Byars, *Technology Advances in Vaccine Development* 401, 1988 (which describes cell mediated immunity using SAF); Epstein et al., 4 *Advance Drug Delivery Reviews* 223, 1990 (which provides an overview of various adjuvants used in preparation of vaccines); Allison and Byars, 95 *J. Immunological Methods* 157, 1986 (which states that the addition of the muramyl dipeptide to the adjuvant markedly augments cell mediated responses to a variety of antigens, including monoclonal immunoglobulins and virus antigens); and Morgan et al., 29 *J. Medical Virology* 74, 1989 (which describes use of SAF-1 for preparation of a vaccine for Epstein-Barr virus).

Kwak et al., *Idiotype Networks in Biology and Medicine*, Elsevier Science Publishers, p. 163, 1990 (not admitted to be prior art to the present application) describe use of SAF without muramyl dipeptide as an adjuvant for a B-cell lymphoma idiotype in a human. Specifically, an emulsion of Pluronic L121, squalane, and 0.4% TWEEN-80 in phosphate buffered saline was administered with the idiotype. They state that "[a]ddition of an adjuvant should further augment . . . humoral responses, and may facilitate induction of cellular responses as well.

Other immunological preparations include liposomes (Allison et al., U.S. Pat. Nos. 4,053,585, and 4,117,113); cyclic peptides (Dreesman et al., U.S. Pat. No. 4,778,784); Freunds Complete Adjuvant (Asherson et al., 22 *Immunology* 465, 1972; Berman et al., 2 *International J. Cancer* 539, 1967; Allison, 18 *Immunopotentiation* 73, 1973; and Allison, *Non-Specific Factors Influencing Host Resistance* 247, 1973); ISCOMs (Letvin et al., 87 *Vaccines* 209, 1987); adjuvants containing non-ionic block polymer agents formed with mineral oil, a surface active agent and TWEEN 80 (Hunter and Bennett, 133 *J. Immunology* 3167, 1984; and Hunter et al., 127 *J. Immunology* 1244, 1981); adjuvants composed of mineral oil and emulsifying agent with or without killed mycobacteria (Sanchez-Pescador et al., 141 *J. Immunology* 1720, 1988); and other adjuvants such as a lipophilic derivative of muramyl tripeptide, and a muramyl dipeptide covalently conjugated to recombinant protein (id.).

SUMMARY OF THE INVENTION

Applicant has discovered a safe and advantageous method and compositions by which CTL responses may be induced in humans and domesticated or agriculturally important animals. The method involves the use of an antigen formulation which has little or no toxicity to animals, and lacks an immunostimulating peptide, (e.g., muramyl dipeptide) the presence of which would decrease the desired cellular response. In addition, the methodology is simple to use and does not require extensive in vivo work to alter existing cells by recombinant DNA techniques to make them more antigenic. This discovery is surprising since it was unexpected that such a CTL response could be induced by use of such an antigen formulation lacking immunostimulating peptides or their equivalent. Applicant's findings allow the use of such antigen formulations in a broad spectrum of disease states, or as a prophylactic agent. For example, such antigen formulation administration can be used for the treatment of viral diseases in which a CTL response is important, for example, in the treatment of HIV infection or influenza; it can also be extended to use in treatment of bacterial infections, cancer, parasitic infections, and the like. As a prophylactic agent, the antigen formulation combined with a suitable antigen is useful in prevention of infection by viruses responsible for the aforementioned viral diseases, particularly the treatment of HIV infection, and also for treatment of patients at risk of cancer, for example, after resection of a primary tumor.

Thus, in a first aspect the invention features a method for inducing a CTL response in a human or domesticated (e.g., a cat or dog) or agriculturally important animal (e.g., a horse, cow or pig) to an antigen other than B-cell lymphoma antigen or egg albumin. The method includes the steps of providing the antigen to which the CTL response is desired, and providing a non-toxic antigen formulation which comprises, consists, or consists essentially of, a stabilizing detergent, a micelle-forming agent, and a biodegradable and biocompatible oil. This antigen formulation preferably lacks any immunostimulating peptide component, or has sufficiently low levels of such a component that the desired cellular response is not diminished. This formulation is preferably provided as a stable oil-in-water emulsion. That is, each of the various components are chosen such that the emulsion will remain in an emulsion state for a period of at least one month, and preferably for more than one year, without phase separation. In the method the antigen and antigen formulation are mixed together to form a mixture (preferably by microfluidization), and that mixture administered to the animal in an amount sufficient to induce CTL response in the animal. Such administration is required only once.

By "stabilizing detergent" is meant a detergent that allows the components of the emulsion to remain as a stable emulsion. Such detergents include polysorbate, 80 (TWEEN) (Sorbitan-mono-9-octadecenoate-poly(oxy-1,2-ethanediyl; manufactured by ICI Americas, Wilmington, Del.) TWEEN 40, TWEEN 20, TWEEN 60, Zwittergent 3–12, TEEPOL HB7, and SPAN 85. These detergents are usually provided in an amount of approximately 0.05 to 0.5%, preferably at about 0.2%.

By "micelle-forming agent" is meant an agent which is able to stabilize the emulsion formed with the other components such that a micelle-like structure is formed. Such agents preferably cause some irritation at the site of injection in order to recruit macrophages to enhance the cellular response. Examples of such agents include polymer surfactants described by BASF Wyandotte publications, e.g., Schmolka, 54 *J. Am. Oil. Chem. Soc.* 110, 1977, and Hunter et al., 129 *J. Immunol* 1244, 1981, both hereby incorporated by reference, PLURONIC L62LF, L101, and L64, PEG1000, and TETRONIC 1501, 150R1, 701, 901, 1301, and 130R1. The chemical structures of such agents are well known in the art. Preferably, the agent is chosen to have a hydrophile-lipophile balance (HLB) of between 0 and 2, as defined by Hunter and Bennett, 133 *Journal of Immunology* 3167, 1984. The agent is preferably provided in an amount between 0.5 and 10%, most preferably in an amount between 1.25 and 5%.

The oil is chosen to promote the retention of the antigen in oil-in-water emulsion, i.e., to provide a vehicle for the desired antigen, and preferably has a melting temperature of less than 65° C. such that emulsion is formed either at room temperature (about 20° C. to 25° C.), or once the temperature of the emulsion is brought down to room temperature. Examples of such oils include squalene, squalane, EICOSANE, tetratetracontane, glycerol, and peanut oil or other vegetable oils. The oil is preferably provided in an amount between 1 and 10%, most preferably between 2.5 and 5%. It is important that the oil is biodegradable and biocompatible so that the body can break down the oil over time, and so that no adverse affects, such as granulomas, are evident upon use of the oil.

It is important in the above formulation that a peptide component, especially a muramyl dipeptide (MDP) be lacking. Such a peptide will interfere with induction of a CTL response if it provided in an amount greater than about 20 micrograms per normal human formulation administration. It is preferred that such peptides be completely absent from the antigen formulation, despite their apparent stimulation of the humoral compartment of the immune system. That is, applicant has found that, although such peptides may enhance the humoral response, they are disadvantageous when a cytotoxic T-lymphocyte response is desired.

In other related aspects, the antigen formulation is formed from only two of the above three components and used with any desired antigen (which term includes proteins, polypeptides, and fragments thereof which are immunogenic) except egg albumin (or other albumins, e.g., HSA, BSA and ovalbumin), to induce a CTL response in the above animals or humans.

Applicant believes that the above formulations are significantly advantageous over prior formulations (including ISCOMs, DETOX, and SAF) for use in humans. Unlike such formulations, the present formulation both includes a micelle-forming agent, and has no pentides, cell wall skeletons, or bacterial cell components. The present formulation also induces a CTL response which either does not occur with the prior formulations, or is significantly enhanced compared to those formulations.

By "non-toxic" is meant that little or no side effect of the antigen formulation is observed in the treated animal or human. Those of ordinary skill in the medical or veterinary arts will recognize that this term has a broad meaning. For example, in a substantially healthy animal or human only slight toxicity may be tolerated, whereas in a human suffering from an imminently terminal disease substantially more toxicity may be tolerated.

In preferred embodiments, the antigen formulation consists essentially of two or three of the detergent, agent, and oil; the method consists essentially of a single administration of the mixture (antigen plus antigen formulation) to the human or the animal; the human or animal is infected with a virus and suffers one or more symptoms (as generally defined by medical doctors in the relevant field) of infection from the virus; and the antigen formulation is non-toxic to the human or animal.

In other preferred embodiments, the antigen is chosen from antigenic portions of the HIV antigens: gp160, gag, pol, Nef, Tat, and Rev; the malaria antigens: CS protein and Sporozoite surface protein 2; the Hepatitis B surface antigens: Pre-S1, Pre-S2, HBc Ag, and HBe Ag; the influenza antigens: HA, NP and NA; Hepatitis A surface antigens; the Herpes virus antigens: EBV gp340, EBV gp85, HSV gB, HSV gD, HSV gH, HSV early protein product, cytomegalovirus gB, cytomegalovirus gH, and IE protein gP72; the respiratory syncytial virus antigens: F protein, G protein, and N protein; and the tumor antigens carcinoma CEA, carcinoma associated mucin, carcinoma P21, carcinoma P53, melanoma MPG, melanoma p97, and carcinoma Neu oncogene product, carcinoma p53 gene product, and mutated p21 ras protein presented in a variety of malignant tumors.

In related aspect, the invention features a composition comprising, consisting, or consisting essentially of an antigen mixed with an antigen formulation described above, and the antigen is chosen from those antigenic portions listed above.

In other related aspects, the invention features methods of treating a patient infected with HIV virus, suffering from malaria, suffering from influenza, suffering from hepatitis, suffering from a cancer, infected with herpes virus, or infected with respiratory syncytial virus, by administering a composition including an appropriate antigen (e.g., selected from those listed above) mixed with one of the above antigen formulations.

Other features and advantages of the invention will be apparent from the following description of the preferred embodiments thereof, and from the claims.

DESCRIPTION OF THE PREFERRED EMBODIMENTS

The drawings will first briefly be described. Drawings

FIGS. 1A–1C and 4A–4C are graphical presentations of data comparing CTL induction by various ovalbumin formulations; E:T represents effector to target ratio in all Figures.

ANTIGEN FORMULATION

Figure 2B:
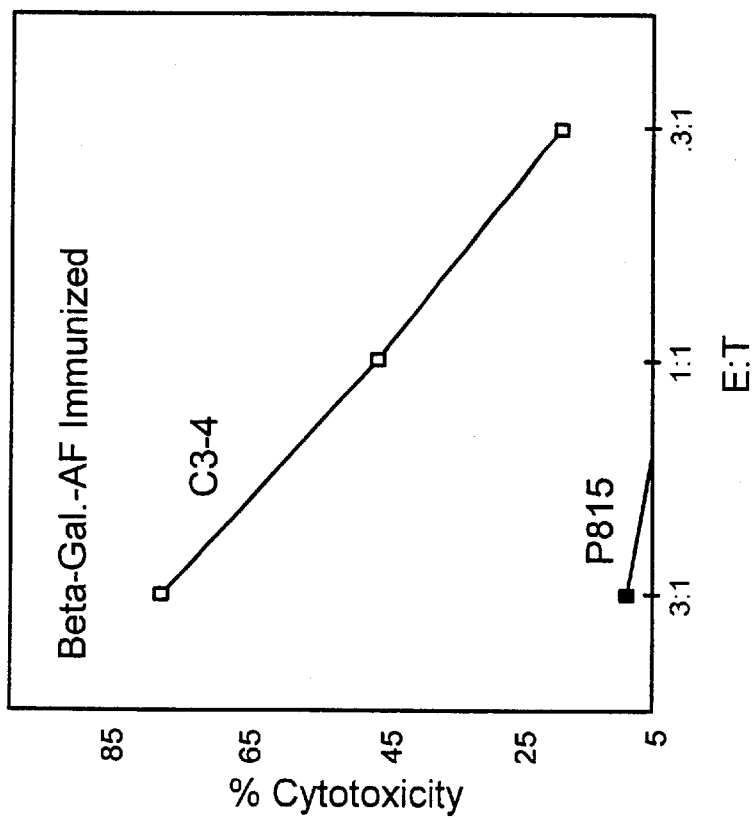
FIGS. 2A and 2B are graphical presentations of data comparing CTL induction by various β-galactosidase formulations.

Antigen formulations useful in this invention are generally described above. Those of ordinary skill in this art will recognize that equivalent Formulations are readily prepared and can be expected to have equivalent properties in induction of a CTL response. Such Formulations are readily tested for their properties using techniques equivalent to those described in the examples below.

There follow examples of the invention with the use of an antigen formulation (AF) composed of about 2.5% squalane, 5% pluronic acid, and TWEEN 80 in a phosphate buffered saline. Specifically, an emulsion of the AF included: 15 mg squalane, 37.5 mg poloxamer 401 (PLURONIC L121), 6 mg polysorbate 80 (TWEEN 80), 0.184 mg potassium chloride, 0.552 mg potassium phosphate monobasic, 7.36 mg. sodium chloride, 3.3 mg sodium phosphate dibasic (anhydrous), per 1 ml water, pH 7.4. This emulsion was microfluidized using standard technique (Microfluidics Model M110F) with a back-pressure module at 11–14,000 psi with gradual return to atmosphere pressure, cooling and packing in wet ice.

In other examples, antigen was mixed with the microfluidized squalane (S), pluronic (P) and Tween 80 (T) mixture to achieve a final concentration of 0.2% Tween 80, 1.25% pluronic, and 5% squalane respectively. To determine the sub-components necessary for an antigen specific immune response induction, squalane-Tween 80, pluronic-Tween 80 or squalane-pluronic were prepared at the same concentration as for the three components mixture. Pluronic, squalane or Tween 80 was also prepared individually to determine the effect of individual component on the CTL induction. Substitutions of Tween 20, Tween 40 or Zwittergent for Tween 80 were also made to determine the effect of various Tween derivative on the CTL induction in the ova system. Substitutions of squalane in the three component formulation were made with Eicosone or Triacontone and substitution for the co-polymer pluronic in the same three components formulation were made by PEG 1000, Pleuronic L62LF, and the Tetronics 1501 and 150R1. As two component formulations, various analogs in various combinations were mixed and tested for ova specific CTL induction. They are a mixture of cholesterol—Tween 80, squalane—Tween 20, Pristane—Tween 80 or olive oil—Tween 80. For a stabilization study, the microfluidized mixture of squalane-Tween 80 was mixed with dextrose to a final concentration of 5%. In all cases the combinations of excipients were mixed in a microfluidizer to made a stable emulsion. In some experiments, two components formulations were mixed with various concentration of MDP for CTL and humoral response inductions. Table 1 describes a comprehensive list of various formulations used in this study.

TABLE 1

Effect of various substitution in three or two component systems

| | percent kill at E:T 100:1 |
|---|---|
| Substitution in three component formulations | |
| STP | 84 |
| Tween 40 (T) | 66 |
| Tween 20 (T) | 48 |
| T1501 (P) | 0 |
| T150RI (P) | 0 |
| Pluronic L62LF (P) | 47 |
| Eicosane (S) | * |
| PEG1000 (P) | * |
| Triacontane (S) | * |
| Zwittergent (T) | * |
| Substitution in two component formulations | |
| ST | 76 |
| PT | 45 |
| SP | 26 |
| Cholesterol (S) + Tween 80 | 0 |
| Squalane + Tween 29 (T) | 65 |
| Pristane (S) + Tween 80 | 42 |
| Olive Oil (S) + Tween 80 | 69 |
| 1 component formulation | |
| Pluronic L121 | 0 |
| Squalane | 0 |
| Tween 80 | 0 |
| Squalane + Tween 80 + 5% dextrose | 86 |

*CTL assay is being repeated

Syntex adjuvant formulation (microfluidized; SAFm) was used as an adjuvant control and consists of two parts. Part I consists of phosphate buffered saline containing a final concentration of 5% squalane, 1.25% pluronic and 0.2% Tween 80 (vehicle or I-SAF). Part II consists of N-Acetylmuramyl-L-Threonyl-D-Isoglutamine (Thr-MDP), a derivative of mycobacterium cell wall component. For immunization purposes, antigen is mixed with microfluidized vehicle (part I) to obtain a homogeneous emulsion. MDP is added to made SAFm, and vortexed briefly. The MDP concentration in the mixture was varied to determine if there was an optimum concentration for CTL induction. As an adjuvant control, mice were also immunized with soluble antigens mixed with alum according to the manufacture's manual (Pierce Chemical, Rockford, Ill.) or with Complete Freund's Adjuvant (CFA).

This antigen formulation is used for induction of cytotoxic T-lymphocyte responses in mice. Those of ordinary skill in the art will recognize that such a mouse model is indicative that equivalent experiments or treatments will similarly induce cytotoxic T-lymphocyte responses in humans, domesticated, or agricultural animals. The amount of antigen formulation and antigen useful to produce the desired cellular response may be determined empirically by standard procedures, well known to those of ordinary skill in the art, without undue experimentation. Thus, if desired to minimize the side effect of treatment with such a mixture those of ordinary skill in the art may determine a minimum level of such a mixture for administration to a human, domesticated, or agricultural animal in order to elicit a CTL response, and thereby induce immunity to a desired antigen. In normal use, such a mixture will be injected by any one of a number of standard procedures, but particularly preferred is an intramuscular injection at a location which will allow the emulsion to remain in a stable form for a period of several days or several weeks.

Methods

The following materials and methods were used in the examples provided below unless otherwise noted:

Mice

Female C57BL/6 (H-$2^b$) and BALB/c (H-$2^d$) mice were purchased from Harlen Sprague (San Diego, Calif.).

Antigens

Ovalbumin (OVA, Grade VI; Sigma Chemical Co., St. Louis, Mo.) was used in the native form. β-galactosidase, (β-gal, Grade VIII; BRL) was used in the native form and after boiling in 1 M NaOH for 2 min to give an alkali digest. Recombinant gp120 was purchased from American Biotechnology.

Tumor Cells and Transfectants

The tumor cells used were the Ia lines EL4 (C57BL/6, H-$2^b$ thymoma) and P815 (DBA/2, H-$2^d$ mastocytoma). Derivation of the OVA-producing EL4 transfectant, EG7-OVA, is described previously by Moore et al., 54 Cell 777, 1988. The β-gal-producing transfectant, P13.1, was derived by electroporation of $10^7$ P815 cells in 1 ml of phosphate buffered saline (PBS) with 10 mg of PstI linearized pCH110 (Pharmacia LKB Biotechnology Inc., Piscataway, N.J.) and 1 mg of PvuI linearized pSV2 neo (Southern et al., 1 J. Mol. Appl. Genet. 327, 1982) followed by selection in 400 μg/ml of the antibiotic G418. The C3–4 transfectant was derived from the BALB/c hybridoma Igm 662 by transfecting with a plasmid encoding the β-gal gene fused to the third and fourth exon of IgM heavy chain (Rammensee et al., 30 Immunogenetics 296, 1989). The gp160IIIb expressing 3T3 fibroblast, 15–12, was provided by Dr. Germain of NIH (Bethesda, Md.). The $K^b$ transfected L cell line was provided by Dr. Carbone, Monash University, Australia. The $D^d$ and $L^d$ transfected L cell lines were provided by Dr. Ted Hensen, Washington University, St. Louis.

Immunization

Mice were immunized intravenously with a 200 μl suspension of 25×$10^6$ splenocytes, after a cytoplasmic loading as described by Moore et. al. supra, and Carbone et al., J. Exp. Med. 169:603, 1989). For OVA-antigen formulation or β-gal-antigen formulation immunization, 30 μg of each protein antigen was injected per mouse in the footpad and the tailbase subcutaneously. Each injection consists of 67 μl of microfluidized antigen formulation (made following standard procedures) and 30 μg of protein antigen in a final volume of 200 μl. The final volume was made up with HBSS, see, Whittaker manual (Welkersville, Md.). MDP was provided in concentrations between 0 and 300 μg. Where stated, mice were immunized with soluble antigens in CFA, or in alum in a total volume of 200 μl.

In vitro stimulation of effector populations

Spleen cells (30×10⁶) from normal or immunized mice which had been primed at least 14 days earlier were incubated with 1.5×10⁶ EG7-OVA (irradiated with 20,000 rad) for OVA responses or 1.5×10⁶ C3-4 cells (irradiated with 20,000 rad) for β-gal response in 24 well plates at 37° C. in 7% $CO_2$/air. All the tissue cultures were performed in a complete medium consisting of IMDM medium, see, Whittaker Manual (Welkersville, Md.) supplemented with 10% fetal calf serum (FCS), 2 mM glutamine, gentamycin and 2×10⁻⁵ M 2-mercaptoethanol. For the in vitro depletion experiments, in vivo primed or in vitro stimulated spleen cells were treated with monoclonal antibodies (mAbs) RL.172 (anti-CD4) or mAbs 3.168 (anti-CD8) for removal of CD4⁺ or CD8⁺ T cells (Sarmiento et al., 125 *J. Immunol.* 2665, 1980, and Ceredig et al., 314 *Nature* 98, 1985). The mAb RL.172 and mAb 3.168 were obtained from Dr. Jonathan Sprent at Scripps Clinic and Research Foundation.

Spleen cells (30×10⁶) from normal or immunized mice which had been primed at least 21 days earlier were incubated with 1.5×10⁶ 15-12 (treated with 200 ug of mitomycin C for 45 minutes per 10⁸ cells) or with 500 μg of 18IIIB peptide containing the dominant CTL epitope in Balb/c mice in complete IMDM media (Irvine Scientific, Santa Ana, Calif.) containing 10% pre-screened FCS (ICN Flow; ICN Biochemicals, Inc., Costa Mesa, Calif.), 2 mM glutamine, gentamycin and 2×10⁻⁵ M 2-mercaptoethanol. For in vitro stimulation with peptides, spleen cells were cultured in complete IMDM containing 5% conA supernatant.

For depletion experiments, in vivo primed or in vitro stimulated spleen cells were treated with mAbs RL.172 (anti-CD4) or mAbs 3.168 (anti-CD8) in presence of low tox. rabbit complement (Cederlane Laboratories, Ltd., Hornby Ontario, Canada) for removal of CD4⁺ or CD8⁺ T cells (22, 23). The mAb RL.172 and mAb 3.168 were a gift from Dr. Jonathan Sprent at Scripps Clinic and Research Foundation.

Cytoxicity Assay

Target cells (1×10⁶) were labeled with 100 μCi [$^{51}$Cr] sodium chromate for 60 min. For pecptide pulsed targets, 50 μl of a 1 mg/ml peptide solution in HBSS was added during the targets labeling with $^{51}$Cr. After washing, 10⁴ labeled targets and serial dilutions of effector cells were incubated in 200 ml of RP10 for 4 h at 37° C. 100 μl of supernatant was collected and the specific lysis was determined as: Percent specific lysis=100×{(release by CTL−spontaneous release)/(maximal release−spontaneous release)}. Spontaneous release in the absence of cytotoxic T-lymphocyte (CTL) was <25% of maximal release by detergent in all experiments.

Determination of Antibody Responses in Mice and Monkeys

Each well of 96 well, U bottomed plates (Costar, Cambridge, Mass.) were coated with 150 ng of ova or gp120 in 50 ul of HBSS and incubated overnight at 4° C. For the determination of anti-gp120 and anti-ova antibody responses in mice, plates were blocked with 1% BSA for 1 hr. Serially diluted sera were added in 25 μl volume per well and incubated for 2 hrs. Plates were washed and 50 μl of 1:1000 dilution of goat anti-mouse IgG conjugated to HRPO (SBT, Alabama) in 1% BSA were added per well. After 1 hr of incubation, plates were washed and 100 μl of substrate was added per well. The $OD_{405}$ was taken after 10 to 15 minutes. For the determination of monkey anti-gp120 antibody response, all the steps were the same except both the blocking of plates and the dilution of sera were done in 5% normal goat serum in Hank's balanced salt solution.

Peptide Synthesis

Synthetic peptides corresponding to amino acid sequences 253–276 (Sequence Listing No. 1: EQLESIIN-FEKLTEWTSSNVMEER; where the standard one letter code is used to represent each amino acid) of the ovalbumin (Ova 253–276), amino acid sequences 84–102 or the myelin basic protein (MBP 84–102) (Sequence Listing No. 2: DENPVVHFFKNIVTPRTPP), and synthetic peptides corresponding to amino acid sequences 308–322 (18IIIb sequence) of the gp120IIIb, were assembled by solid phase peptide synthesis using an Applied Biosystems 430A synthesizer. Amino acids were coupled via pre-formed symmetric anhydrides with the exception of asparagine, glutamine and arginine which were coupled as hydroxybenzotriazole esters. Coupling efficiency was monitored by ninhydrin reaction following the method of Kaiser et al. 34 *Anal. Biochem.* 595, 1970. The peptides were released from the support with HF following the "low-high" procedure described by Tam, et al. 21 *J. Am. Chem. Soc.* 6442, 1983, and the peptides extracted from the resin with 10% acetic acid. After lyophilization, peptides were desalted on a Sephadex G-25 column, and samples of the peptides then HPLC purified by reverse phase chromatography on a Vydac preparative C-18 column. Purified peptides (98%) were solubilized in HBSS at a final concentration of 10 mg/ml and diluted to the desired concentration in the complete media.

CNBr Digest

Samples of protein (e.g., β-galactosidase) were treated with 100 fold molar excess of cyanogen bromide in a solution of 100 mM trifluoroacetic acid. The reaction was allowed to proceed for 18 hours at room temperature (about 20° C.) with rotation. Following the prescribed reaction time, the peptide fragments were separated from the reactant using a SEP-PAK C-18 apparatus (Waters), eluted with 95% acetonitrile, and lyophilized.

Alkaline digest

Protein samples (e.g., β-galactosidase) were treated with 1 N NaOH and boiled for 2 minutes, and the resulting peptide fragments were separated from the reactants using a C-18 SEP-PAK apparatus (Waters), and eluted with 95% acetonitrile and lyophilized.

EXAMPLE 1

Class I restricted CTL priming

Moore et al., 113 *UCLA Symp. Mol. Cell. Biol.* 1989 and Carbone and Bevan, 171 *J. Exp. Medicine* 377, 1990, demonstrate that mice immunized with spleen cells loaded cytoplasmically with soluble OVA, were primed for OVA specific, class I restricted CTL response. The OVA-expressing EL4 transfectant EG7-OVA was employed for in vitro stimulation of in vivo primed splenic lymphocytes and also used as target for OVA specific CTL mediated killing. This study also demonstrated that CD8⁺ effectors induced by EG7-OVA transfectant or by spleen cells cytoplasmically loaded with OVA, recognize a determinant mapped by the peptide OVA 258–276 in the context of H-2K$^b$, lyse EG7-OVA, and also kill EL4 cells coated with OVA 258–276. Thus, in order to assess whether an endogenous class I restricted CD8⁺ T cell pathway can be induced by a soluble antigen, the above system was used to determine whether certain antigen formulations can be used to drive soluble antigen into a class I restricted pathway.

a) OVA

C57BL/6 mice were immunized once with various amounts of OVA (30 μg–1 mg per mouse) with or without an antigen formulation. Mice were injected at footpads and tailbase subcutaneously. Spleen cells were taken from the immunized mice at least two weeks after the immunizations and in vitro stimulated with the EG7-OVA transfectants. An OVA concentration as low as 30 μg was as effective as 1 mg dose. Therefore, the CTL studies were routinely performed with spleen cells from 30 μg OVA-primed mice. After five days of in vitro culture with EG7-OVA, priming was assessed by the presence of OVA specific effectors capable of lysing EG7-OVA.

Mice injected with soluble OVA in HBSS as high as 1 mg, showed no evidence of CTL priming (FIG. 1A). However mice immunized with 30 μg OVA in the antigen formulation described above (shown as AF in the figures) showed a significant transfectant specific CTL response (FIG. 1C). Furthermore, the extent of EG7-OVA killing by the OVA-AF immunized spleen cells was comparable to that of OVA-loaded spleen cells immunized mice (FIG. 1B).

That the specificity of CTL priming in vivo was antigen specific was shown by the lack of spleen cells from β-galactosidase immunized mice to manifest secondary CTL response in vitro when stimulated with EG7-OVA. No OVA specific CTL induction was observed.

b) β-galactosidase

Similar results were obtained using another soluble protein antigen, β-gal. For assaying β-gal-specific CTL response, the target used was BALB/c derived β-gal-expressing C3–4 transfectant. Immunization of BALB/c mice with soluble β-gal gave background CTL response. Therefore, for the determination of specific CTL response, harvesting was postponed for at least eight weeks before spleen lymphocytes were harvested, and cultured for five days in the presence of irradiated C3–4 transfectants.

Figure 2A:
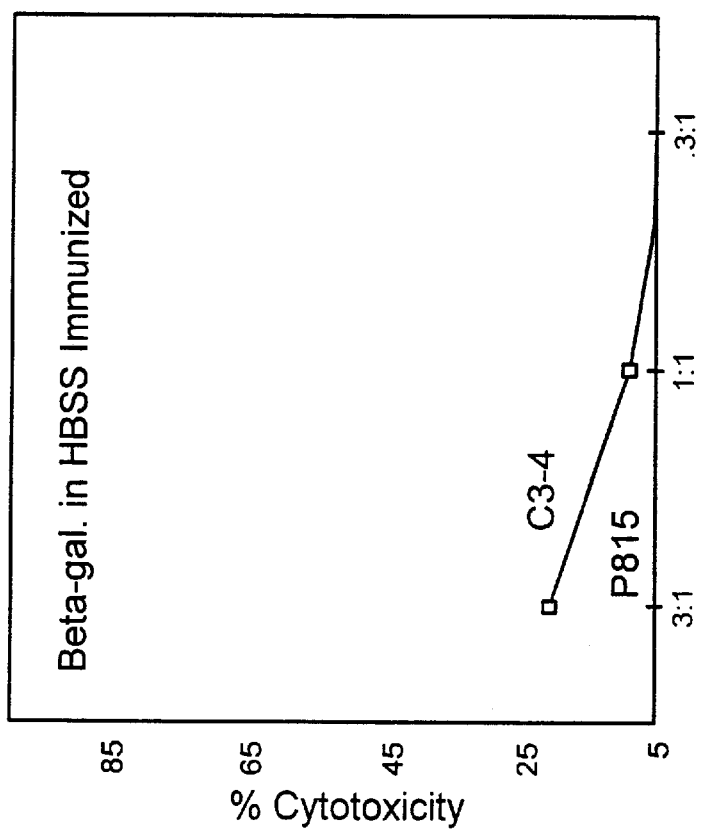

FIG. 2B demonstrates that 30 μg of β-galactosidase in AF induced strong specific CTL response against transfectant. At an effector-to-target (E:T) ratio of 3:1, β-gal-AF immunized mice showed about 80% of specific C3-4 killing. However, only 20% killing of the same target was achieved with effectors isolated from β-gal in HBSS immunized mice at the same E:T ratio (FIG. 2A). Since neither EL4 nor P815 expresses class II MHC gene products and the lysis shows syngeneic restriction, these OVA and β-gal specific effectors are class I MHC restricted.

Figure 3:
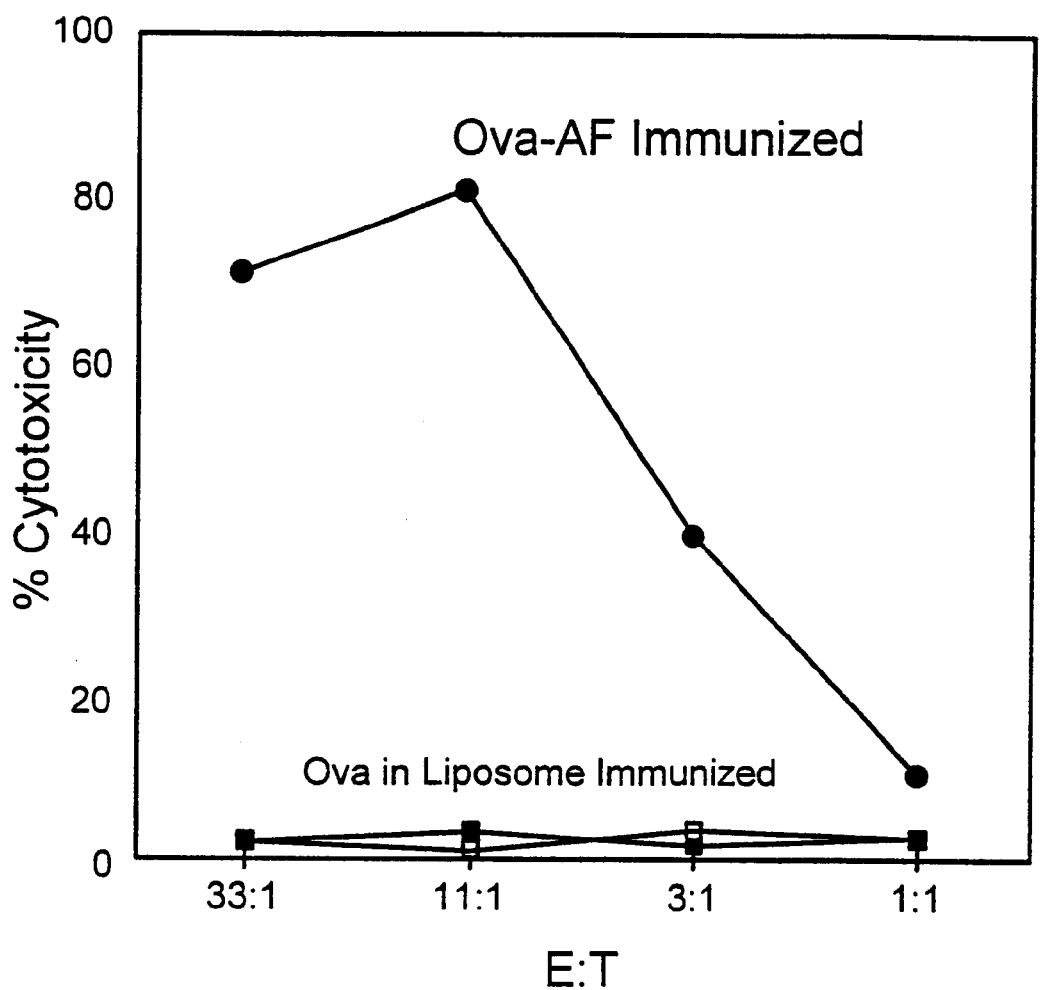
FIG. 3 is a graphical presentation of data comparing CTL induction by ovalbumin in a liposome and in an antigen formulation.

To demonstrate the usefulness of the antigen formulation, mice were immunized with soluble OVA encapsuled in two types of liposomes, one of which was a pH sensitive liposome. One week later, spleen cells were stimulated in vitro, as described above, and tested against $^{51}$Cr-labeled EG7-OVA or EL4. FIG. 3 shows a representative result demonstrating that OVA in liposome could not prime mice for substantial CTL induction. Similar results were observed when OVA was immunized in alum.

EXAMPLE 2

Recognition of epitope by CTL

Figure 4:
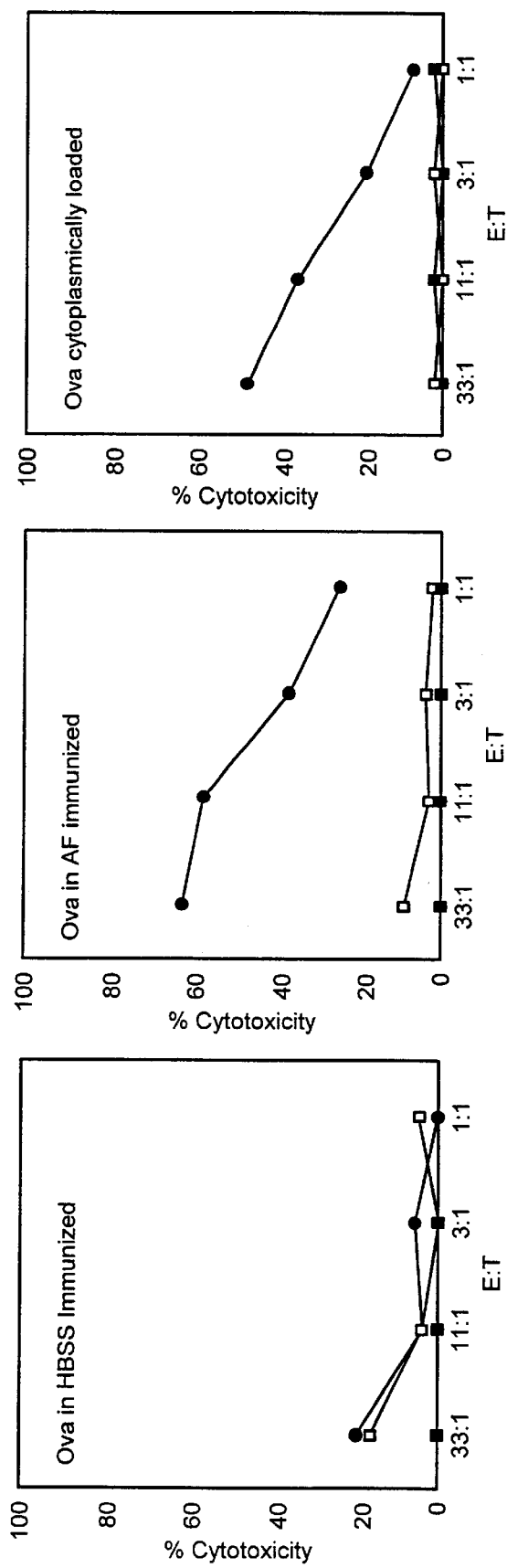

Carbone and Bevan, supra, demonstrated that CTL induced in C57BL/6 mice by EG7-OVA transfectant, and by cytoplasmically OVA-loaded splenocytes recognize EL4 cells coated with the peptide OVA 258–276. To determine whether soluble ovalbumin in AF induces similar CTL responses, spleen cells were prepared from immunized mice and stimulated in vitro with EG7-OVA. The effectors were tested against EL4 cells coated with the peptide OVA 253–276, or with a control peptide derived from myelin basic protein (MBP 84–102). The results demonstrate that OVA-AF primed CTL with a similar specificity to those primed by transfectants, or by cytoplasmically loaded OVA (FIGS. 4A, 4B and 4C). OVA-AF primed effector cells effectively lysed EG7-OVA, and an untransfected EL4 cells coated with 50 μg/10$^8$ cells of OVA peptide, but did not lyse EL4 cells coated with 50 μg/10$^8$ cells of MBP peptide.

In the β-galactosidase system, Carbone and Bevan, supra, indicated that β-gal expressing transfectant and splenocytes cytoplasmically loaded with soluble β-galactosidase, induced CTL which lysed β-gal expressing transfectant and nontransfectant P815 cells coated with alkali digested β-galactosidase. Soluble β-galactosidase induces CTL having similar specificity when immunized in AF (data not shown).

EXAMPLE 3

CTL effectors are CD8$^+$ T cells

Figure 5:
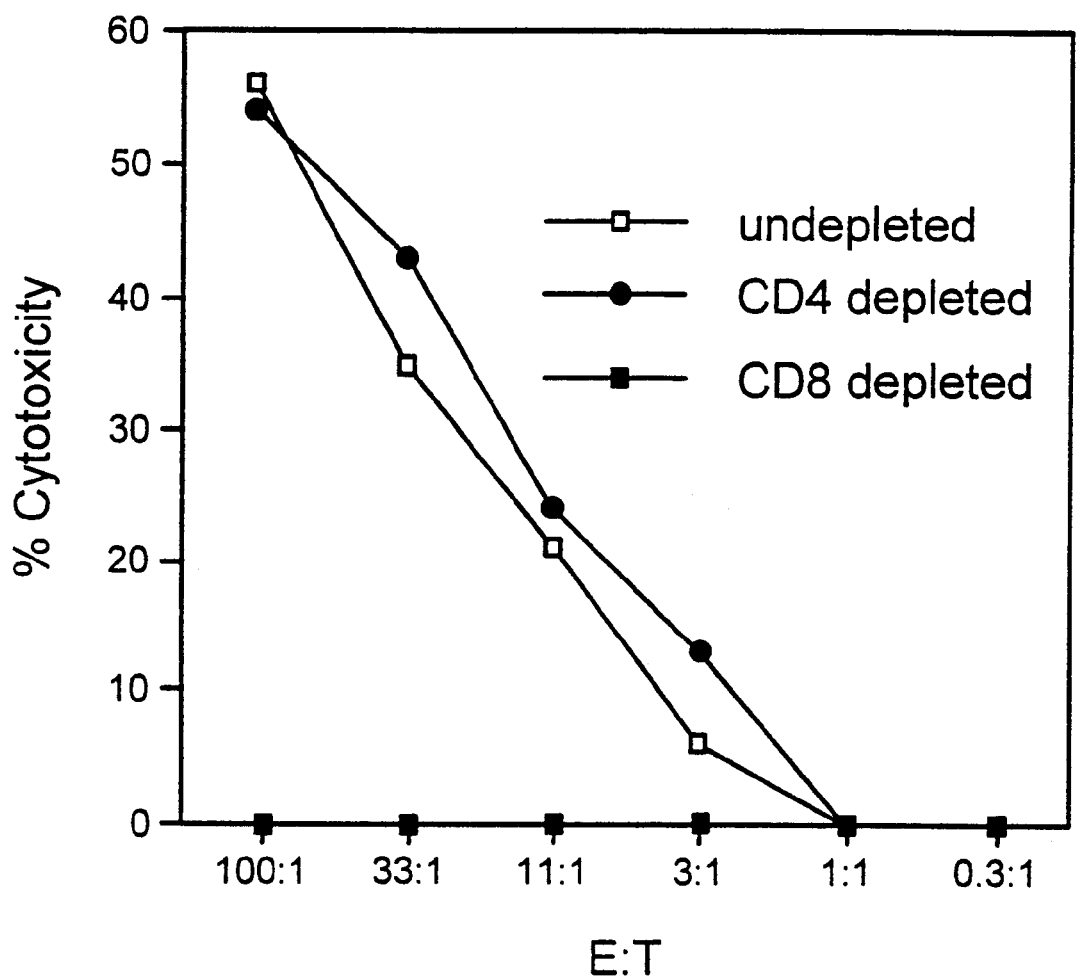
FIGS. 5 and 6 are graphical presentations of data showing the effect of CD4 and CD8 cell depletion on CTL induction.

That soluble protein antigens in AF induce CD8$^+$ effector T cells was shown as follows. Splenocytes from immunized mice were cultured for five days with irradiated transfectants in vitro. Thereafter, cells were harvested and depleted of CD4$^+$ or CD8$^+$ T cells by using monoclonal anti-CD4 or anti-CD8 antibodies plus complement. Depleted populations were then tested against $^{51}$Cr-EG7-OVA in the OVA system or $^{51}$Cr-P13.1 in the β-gal system. The data shown in FIG. 5 indicates that, in the OVA system, depletion of CD8$^+$ T cells abrogated cytolytic activity conferred by the whole effector cell population. However, depletion of CD4$^+$ T cell population did not have any effect on the lysis of EG7-OVA.

Similarly, in the β-gal system, depletion of CD8$^+$ T cells abrogated the cytolytic activity of β-gal-antigen formulation immunized spleen cells.

EXAMPLE 4

Soluble OVA and β-gal in AF crime CD8$^+$ T cells

Figure 6:
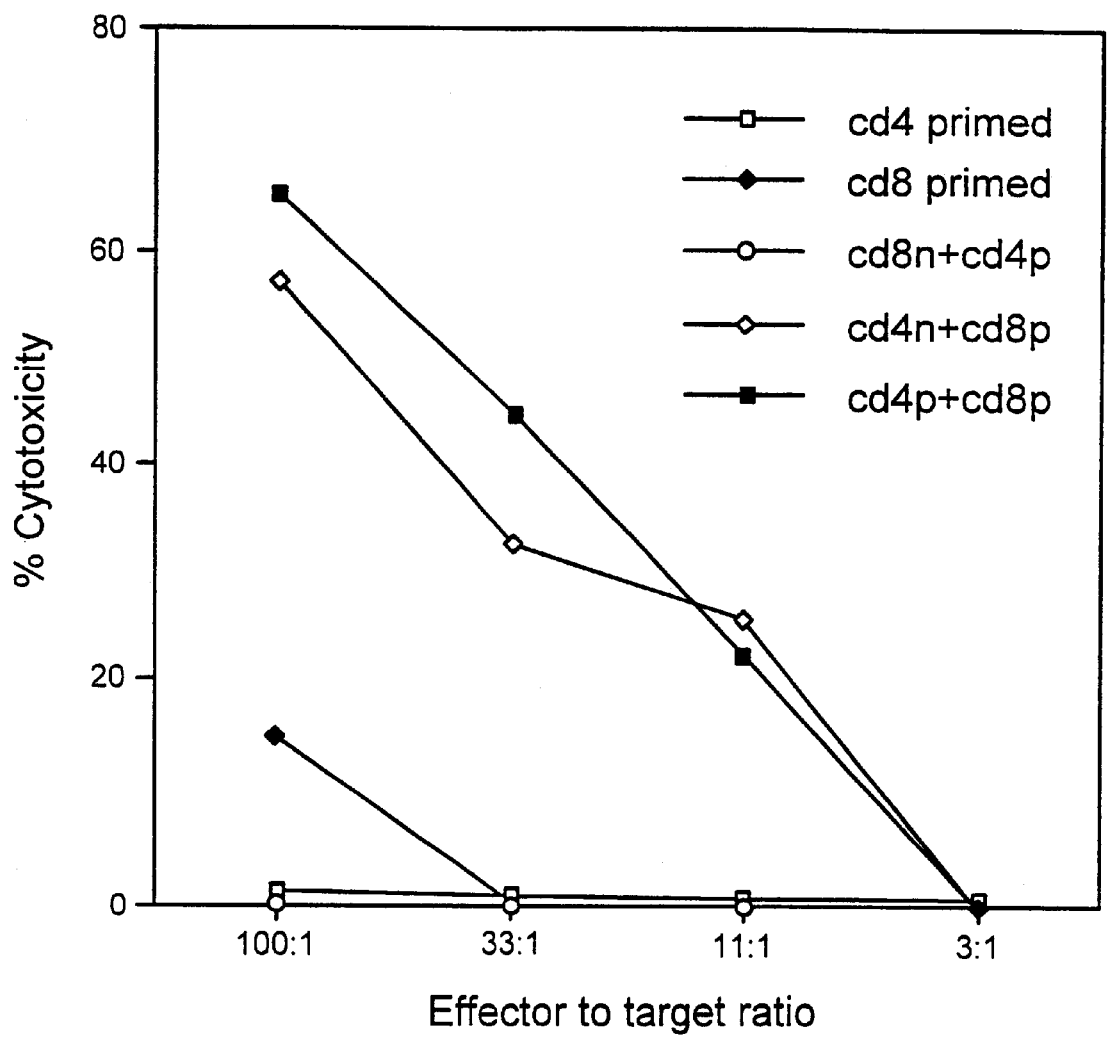

To demonstrate that OVA-AF primes CD8$^+$ T cell populations in vivo, and is critical for in vitro secondary response, CD4$^+$ or CD8$^+$ populations were depleted from spleens of OVA-AF immunized mice and from naive mice. This treated populations were then stimulated in vitro with EG7-OVA alone, or in combination of CD4$^+$ and CD8$^+$ T cells from OVA-AF immunized mice, or in various combination of CD4$^+$ or CD8$^+$ T cells from OVA-AF immunized mice with the CD4$^+$ or CD8$^+$ cells from naive mice. FIG. 6 shows that primed CD8$^+$ cells are essential for the manifestation of a secondary CTL response in vitro. These data also indicate that for the effective secondary CTL response in vitro, CD4$^+$ T cells are required. CD4$^+$ cells are not needed for priming.

Similarly, CD8$^+$ T cells were required for the manifestation of β-gal specific secondary CTL response in vitro.

The above examples demonstrate the effect of the antigen formulation on the induction of class I restricted CTL responses against soluble protein antigens. The antigen formulation mediated soluble antigen induced CTL priming, and is similar in activity to that induced by transfectants and by splenocytes cytoplasmically loaded with soluble OVA or β-gal. In the ovalbumin system, EG7-OVA, cytoplasmically loaded OVA splenocytes, and OVA-AF induced: (a) class I restricted CD8$^+$ CTL; (b) CTL that recognize target sensitized with OVA 253–276 synthetic peptide; and (c) long lived CTL after only one immunization. In the β-galactosidase system, the β-gal-AF induced CTL that recognize β-gal expressing transfectant C3–4, and also the untransfected P815 cells sensitized with alkali digested β-gal. This is analogous to what was observed with CTL induced by immunization with spleen cells cytoplasmically loaded with β-galactosidase. The induction of OVA-specific CTL by antigen formulation is unique because neither OVA encapsulated in a pH sensitive liposome, nor in alum, could induce CTL priming in vivo.

These examples Indicate that the antigen formulation used above, and its equivalents, are useful in human therapy and in vaccine development for the induction of CTL in various cancer and viral diseases.

EXAMPLE 5

This is a specific example to show the use of the above AF on producing class I restricted CTL priming by soluble gp120 from HIV.

Figure 7:
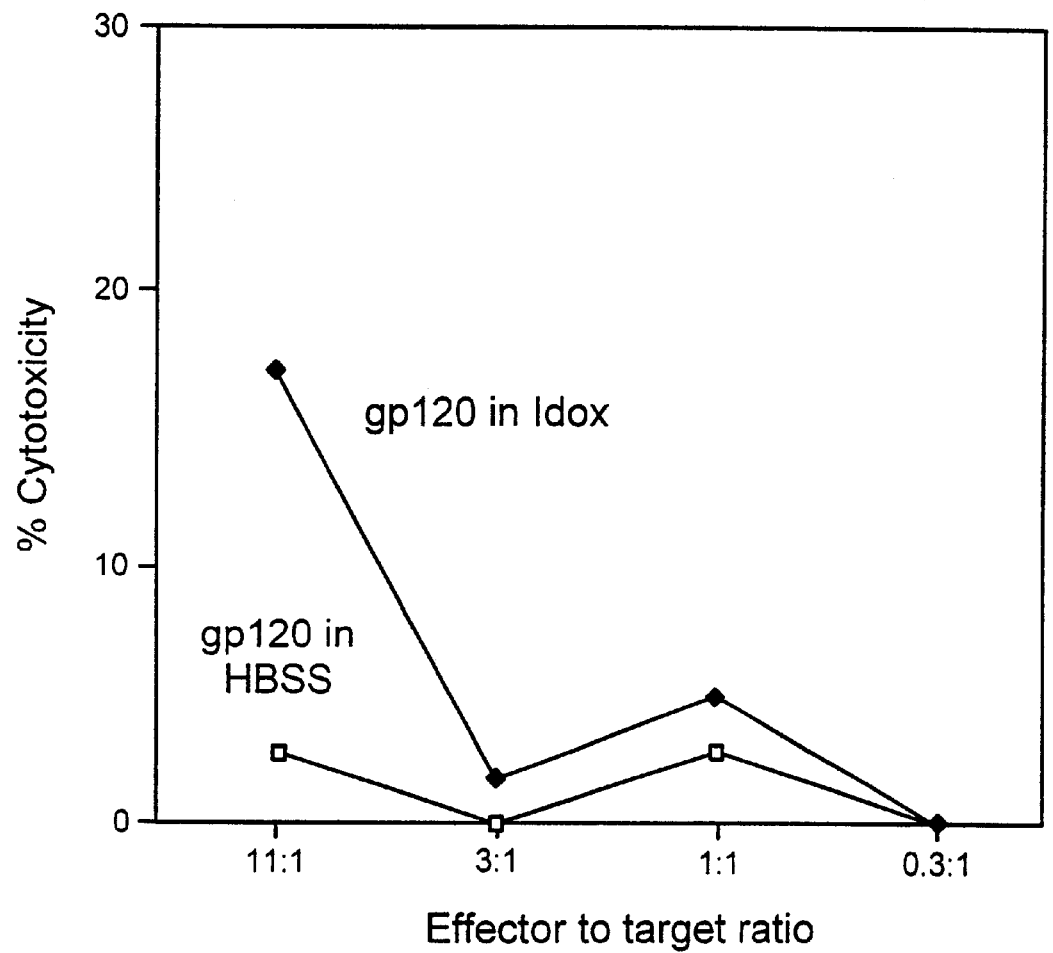
FIG. 7 is a graphical representation of data showing CTL induction by gp120.

The gp160 IIIB expressing cell line was produced in the Balb/c fibroblast-derived 3T3 cell line. It was obtained from Drs. Ron Germain and Jay Berzofsky, National Institute of Health, Bethesda, Md. The gp160 expressing cell line was employed for in vitro stimulation of in vivo primed splenic lymphocytes, and also used as target for gp160 specific CTL induction. Balb/c mice were immunized once with 10 µg of gp160 per mouse with or without AF. Mice were injected at footpads and tailbase subcutaneously. Spleen cells were taken from the immunized mice after two weeks of immunizations and in vitro stimulated with irradiated gp160 transfectants. After five days of culture in vitro, priming was assessed by the presence of specific effectors capable of lysing gp160 transfectants, and not the untransfected cell lines. The results are shown in FIG. 7, where CTL response is potentiated with AF and gp120.

The following example demonstrates the use of antigen formulations of this invention with use of only one or two components. These examples demonstrate that CTL-responses can be induced with only two of the above three components.

EXAMPLE 6

Determination of critical components necessary for CTL induction

To determine whether all the above-noted components are necessary for antigen specific CTL induction, mice were immunized with ovalbumin in a microfluidized formulation of various combination of two of the three components present in the AF above. Two components combinations used were as follows; squalane/Tween in PBS, Squalane/Pluronic in PBS or Pluronic/Tween in PBS. Another set of groups were included where mice were immunized with Ova formulated in a one component system i.e., Squalane in PBS, Pluronic in PBS or Tween in PBS only.

The above three component antigen formulation was modified to exclude one component at a time, substituting PBS in its place.

The above antigen formulation consists of: 0.300 g Tween 80 (Aldrich, Wis.), 1.875 g Pluronic L121 (BASF, N.J.), and 7.5 g Squalane (Aldrich, Wis.), brought to 50 ml with PBS.

The two component formulations were: Squalane/Tween: 0.300 g Tween 80, and 7.5 g Squalane, brought to 50 ml with PBS. Pluronic/Tween: 1.875 g Pluronic L121, and 0.0300 g Tween 80, brought to 50 ml with PBS. Pluronic/Squalane: 1.875 g Pluronic L121, and 7.5 g Squalane, brought to 50 ml with PBS.

The samples were then processed through a microfluidizer, model 110T, Microfluidics Corp, and bottled and stored at 4° C. until use.

Ovalbumin (Sigma, Mo.) was weighed and brought to a 0.3 mg/ml solution in HBSS (Whittaker, supra). The stock 0.3 mg/ml solution was combined with the two component formulations in the following amounts: 5 parts Ovalbumin 0.3 mg/ml solution, 3.3 parts 2 component formulation, and 1.7 part HBSS.

The formulation was vortexed and kept on ice until injected. All solutions were combined just prior to injection.

Each mouse received 200 µl of one formulation containing 30 µl of OVA by injection in both hind footpads and any remaining solution was injected subcutaneously at the tail base. Mice were allowed to rest for two to four weeks prior to spleen harvest.

Figure 8:
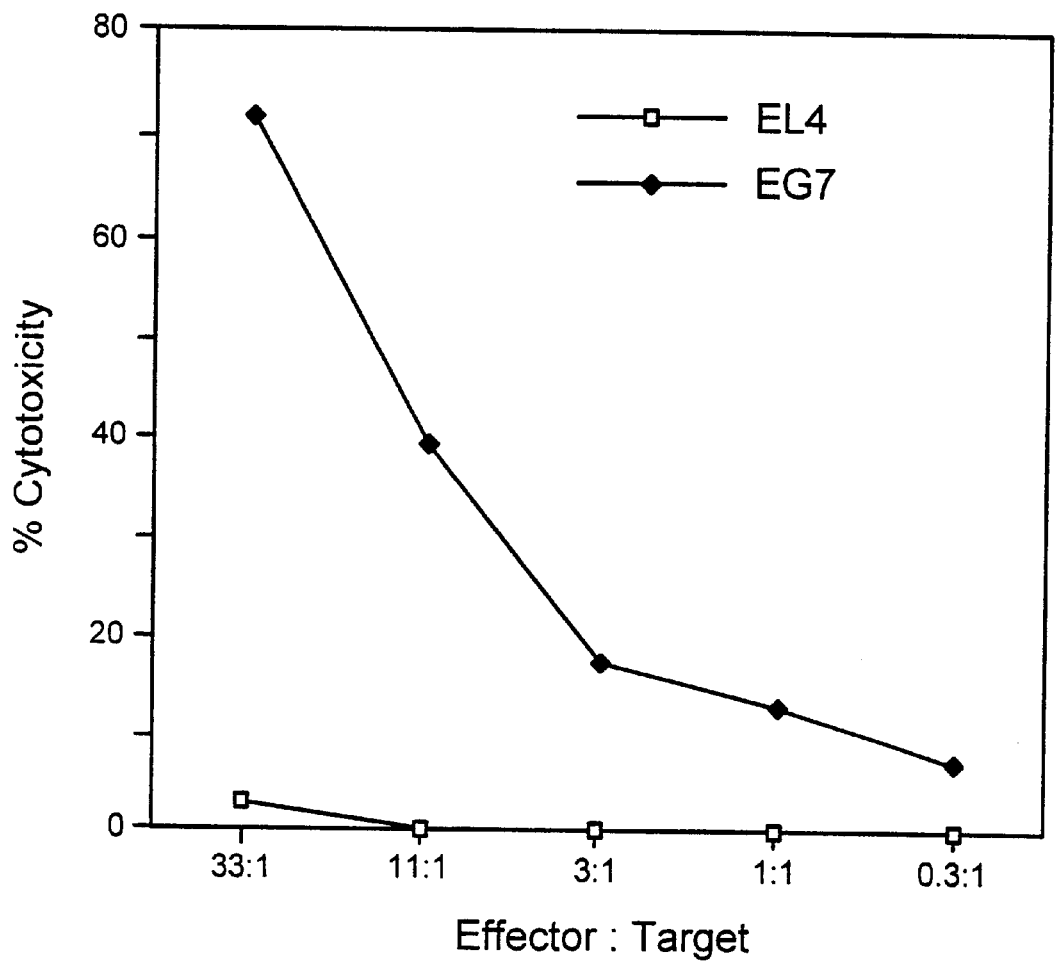
FIG. 8 is a graphical representation of data showing CTL induction by a mixture of pluronic and Tween and an antigen.
Figure 9:
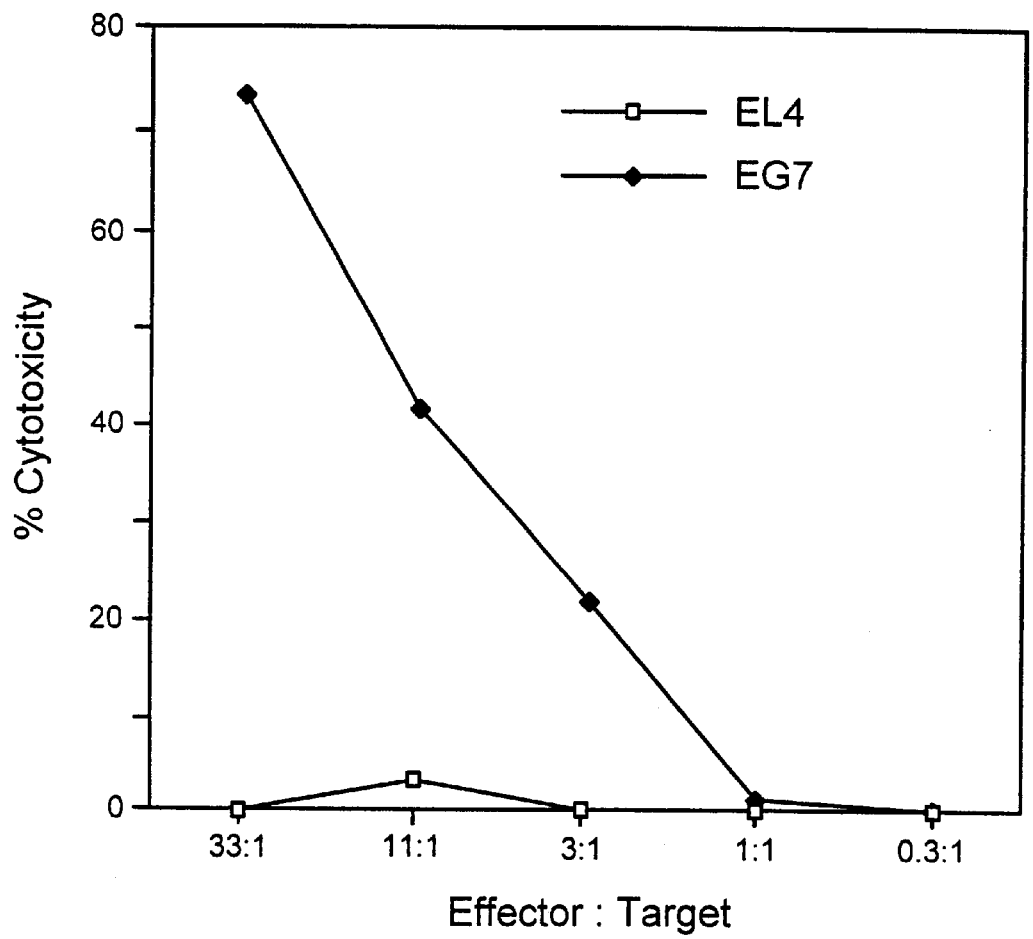
FIG. 9 is a graphical representation of data showing CTL induction with a mixture of by squalane and Tween and an antigen.
Figure 10:
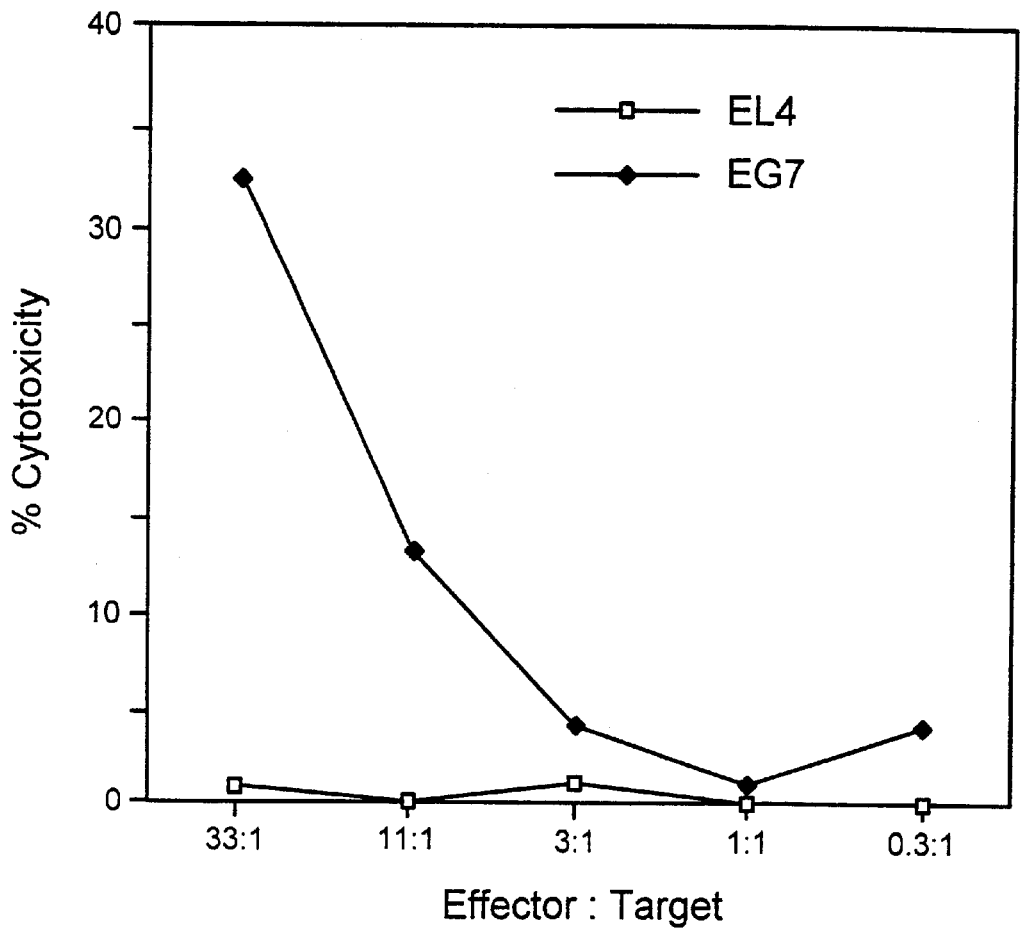
FIG. 10 is a graphical representation of data showing CTL induction by a mixture of squalane and pluronic and an antigen.

Two weeks after immunizations, spleen cells were prepared and in vitro stimulated with irradiated EG7-OVA. After five days of culture, the presence of OVA specific CTL was measured by testing against $^{51}$Cr-EG7-OVA or $^{51}$Cr-EL4 in a 4 hour $^{51}$Cr release assay. The data shown in FIGS. 8–10 demonstrate that Ovalbumin formulated in microfluidized two component system can prime OVA specific CTLs in vivo.

We further evaluated the relative contribution of the individual components for their ability to induce CTL when combined with protein antigens. For immunization purposes soluble antigen was mixed with microfluidized excipients to obtain a stable homogeneous emulsion with particle sizes ranging from 250–300 nm. To further define the components of squalane-Tween 80-pluronic (STP) formulation responsible for CTL induction, we immunized mice with ova in squalane-Tween 80 (ST) mixture, pluronic-Tween 80 (PT) mixture or squalane-pluronic (SP) mixture and as a control, in squalane (S), Tween 80 (T) or pluronic (P). Mice were also immunized with ova-SAFm (containing 70 µg of MDP) or ova-alum as adjuvant controls. For a positive control, mice were immunized with spleen cells cytoplasmically loaded with soluble ova. Other combinations and substitutes were also used and the results are presented in Table 1.

Figure 11:
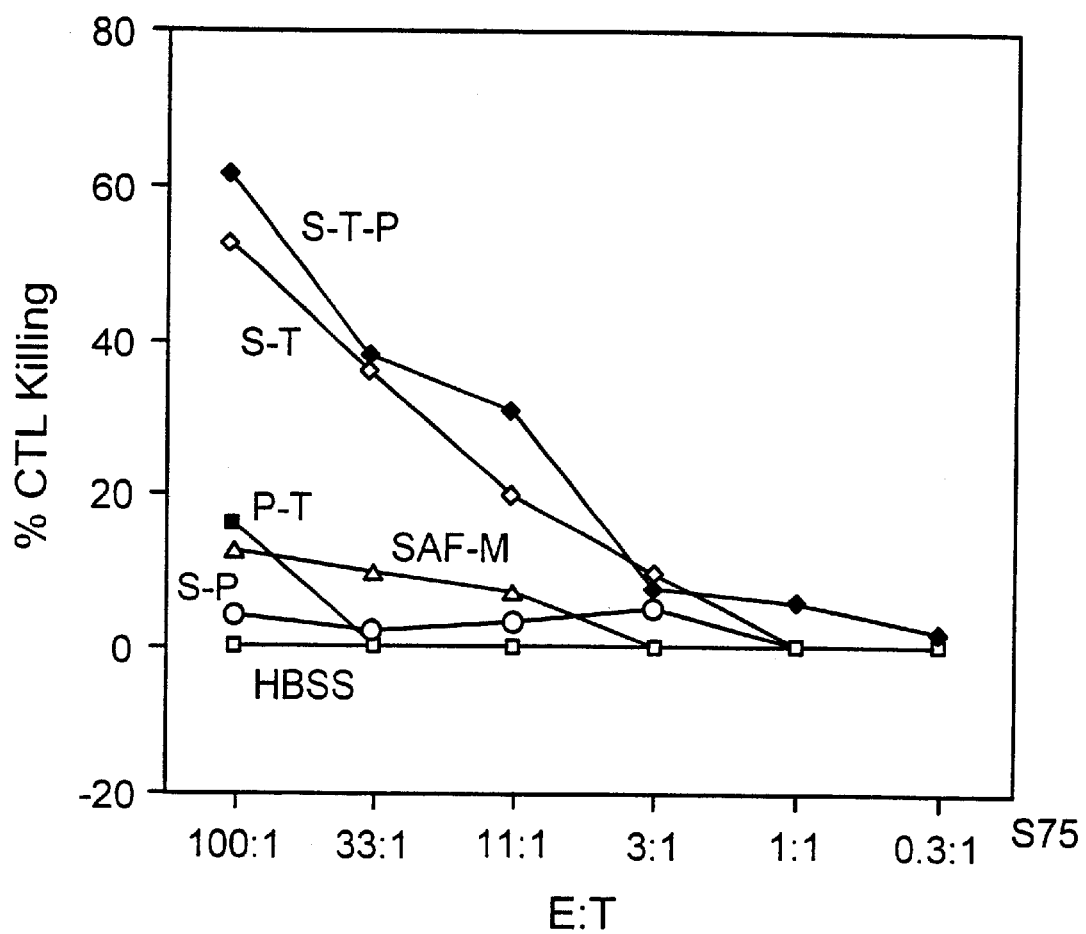
FIG. 11 is a graphical representation of the effect of OVA with various antigen formulations on CTL response.

For the detection of CTL priming studies, mice were immunized once. Two weeks after the immunization, spleen cells were mixed with irradiated EG7-ova (the ova expressing EL4 cells) for five days and tested against $^{51}$Cr-EG7-ova or $^{51}$Cr-EL4 cells. The results (FIG. 11) demonstrate that 30 µg of ova in combination with STP or ST primes class I restricted CTL response in mice. The priming of ova specific CTL by ova in STP or by ova in ST appears to be better than that induced by spleen cells cytoplasmically loaded with soluble ova. Ova in PT or in SP could induce ova specific CTL responses in mice but inconsistently and poorly. Unlike SAFm, the addition of MDP to ST formulation did not compromise the ova specific CTL induction in mice (Table 2). No ova specific CTL induction occurred when mice were immunized with ova mixed with the individual components, S, P or T nor when mice were immunized with ova-SAFm or ova-alum. Mice immunized with as much as 1 mg ova in (a) HBSS, in (b) SAFM or (c) absorbed to alum did not prime ova specific CTL.

TABLE 2

Induction of ova specific CTL response is not blocked by ST + MDP

| | | | % cytotoxicity in mice immunized with* | | | |
|---|---|---|---|---|---|---|
| Stimulator | Target** | E-T | ova-HBSS | ova-ST | ova-ST-MDP 300 µg mouse | ova-ST-MDP 72 µg mouse |
| EG7-ova | EG7-ova | 100:1 | 0 | 100 | 82 | 76 |
| | | 33:1 | 0 | 86 | 67 | 62 |
| | | 11:1 | 0 | 33 | 39 | 25 |
| | | 3:1 | 0 | 0 | 13 | 3 |
| | | 1:1 | 0 | 0 | 0 | 0 |
| | | 3:1 | 0 | 0 | 0 | 0 |

*mice were immunized with 30 µg ova in various formulations

TABLE 2-continued

Induction of ova specific CTL response is not blocked by ST + MDP

% cytotoxicity in mice immunized with*

| Stimulator | Target** | E-T | ova-HBSS | ova-ST | ova-ST-MDP 300 μg mouse | ova-ST-MDP 72 μg mouse |
| --- | --- | --- | --- | --- | --- | --- |

**% specific cytotoxicity against EG7-ova was calculated by subtracting the percent kill against the antigen nonexpressing cell line EL4.

EXAMPLE 7

Components Necessary for ova Specific Antibody Production

Mice were immunized three times at 2 week intervals with 30 μg of ova in HBSS, STP, ST, PT or SP. As a positive control, mice were also immunized with ova-SAFm, as SAFm is known to induce a strong antibody response. Seven days after the second and third immunizations, mice were bled and the sera tested for ova specific antibody response. The results are shown in Table 3. They indicate that mice immunized with ova in STP, ST or in SAFm display similar anti-ova response after two immunizations.

TABLE 3

Induction of anti-ova antibody response

| Immunized with[a] ova in | no. mice responded/ total mice injected | anti-ova antibody titer[b] (1/sera dilution) |
| --- | --- | --- |
| HBSS | 0/3 | <1/20; <1/20; 1/80 |
| STP | 3/3 | <1/15,360; >1/15,360; <1/15,360 |
| ST | 3/3 | 1/3840; 1/15,360; 1/3840 |
| PT | 3/3 | 1/15,360; 1/15,360; 1/3,340 |
| SP | 3/3 | >1/15,360; >1/15,360; >1/15,360 |
| SAFm | 3/3 | >1/15,360; >1/15,360; 1/15,360 |

[a]mice were immunized three times with 30 μg of ova in various formulations
[b]Antibody titer was calculated as the dilution of sera which gave a $OD_{405}$ greater than the $OD_{405}$-2SD obtained with the pre-immune sera.

EXAMPLE 8

HIV gp120 Specific CTL Induction

HIV gp120 IIIB was used as a second antigen system to determine CTL induction in STP, ST or in MP-T. Mice were immunized with 1 μg of gp120 IIIb in HBSS, STP, PT or in ST. As a control, mice were immunized with 1 μg of gp120IIIb in SAFm, CFA (Complete Freund's Adjuvant) or in RIBI adjuvant system containing MPL (monophosphoryl lipid A) and TDM (trihalose dimycolite). Three weeks after the immunization, spleen cells were prepared and stimulated in vitro with mitomycin treated transfectant cells 15–12. After five days of culture, the resultant effector cells were tested against vaccinia:gp160 IIIB, or parental vaccinia infected P815 cells as targets. The results demonstrate that gp120-squalane-Tween 80 formulation and not gp120-Squalane-Tween 80-pluronic formulation or gp120-HBSS induced gp120 specific CTL responses in mice (Table 4).

TABLE 4

Induction of gp120 specific CTL response in mice

| | | | % cytotoxicity in mice immunized with* | | |
| --- | --- | --- | --- | --- | --- |
| Stimulator | Target** | E-T | gp120-HBSS | gp120-ST | gp120-STP |
| 18IIIb/IL2 | vac:gp120 | 100:1 | 23 | 42 | NA*** |
| | | 33:1 | 23 | 38 | NA |
| | | 11:1 | 0 | 0 | NA |
| | | 3:1 | 0 | 35 | NA |
| 18IIIb/IL2 | 15-12 | 100:1 | 0 | 50 | 0 |
| | | 33:1 | 0 | 35 | 0 |
| | | 11:1 | 0 | 27 | 0 |
| | | 3:1 | 0 | 18 | 0 |
| 18IIIb/IL2 | 3T3 + 18IIIb | 100:1 | 0 | 59 | 13 |
| | | 33:1 | 0 | 59 | 2 |
| | | 11:1 | 0 | 57 | 0 |
| | | 3:1 | 0 | 29 | 0 |
| 15-12 | vac:gp120 | 100:1 | 35 | 84 | NA |
| | | 33:1 | 19 | 65 | NA |
| | | 1:1 | 12 | 37 | NA |
| | | 3:1 | 0 | 22 | NA |
| | | 1:1 | 0 | 0 | NA |

*mice were immunized with 1 μg of gp120IIb in various formulations
***% specific cytotoxicity was calculated by subtracting the percent kill against antigen non-expressing cell lines
***NA; not available

EXAMPLE 9

Induction of gp120 Specific Humoral Response in Mice

For the induction of gp120 specific humoral responses, mice were immunized with 1 μg of gp120IIIb three times at two week intervals. The animals were bled and tested for the presence of IgG antibodies detecting gp120IIIb in a solid phase ELISA assay. The results demonstrate that gp120-ST is a better immunogen than gp120-HBSS, gp120SAFm (Table 5), or gp120-STP.

TABLE 5

Induction of anti-gp120 antibody response

| Immunized with[a] gp120 in | no. mice responded/ total mice injected | Anti-gp120 antibody titer[b] (1/sera dilution)* |
| --- | --- | --- |
| HBSS | 0/3 | <1/20, <1/20, <1/20 |
| STP | 1/3 | <1/20, >1/4860, <1/20 |
| ST | 3/3 | >1/4860, >1/4860, >1/4860 |
| PT | 3/3 | >1/4860, >1/4860, >1/4860 |
| SP | 2/3 | <1/20, 1/540, 1/540 |
| SAFm | 2/3 | 1/180, >1/4860, 1/540 |

[a]Mice were immunized with 1 μg of gp120IIIb three times in various formulations.
[b]anti-gp120 antibody titer was calculated as described in Table 3.

EXAMPLE 10 gp120 Specific antibody Responses in monkeys

Figure 12:
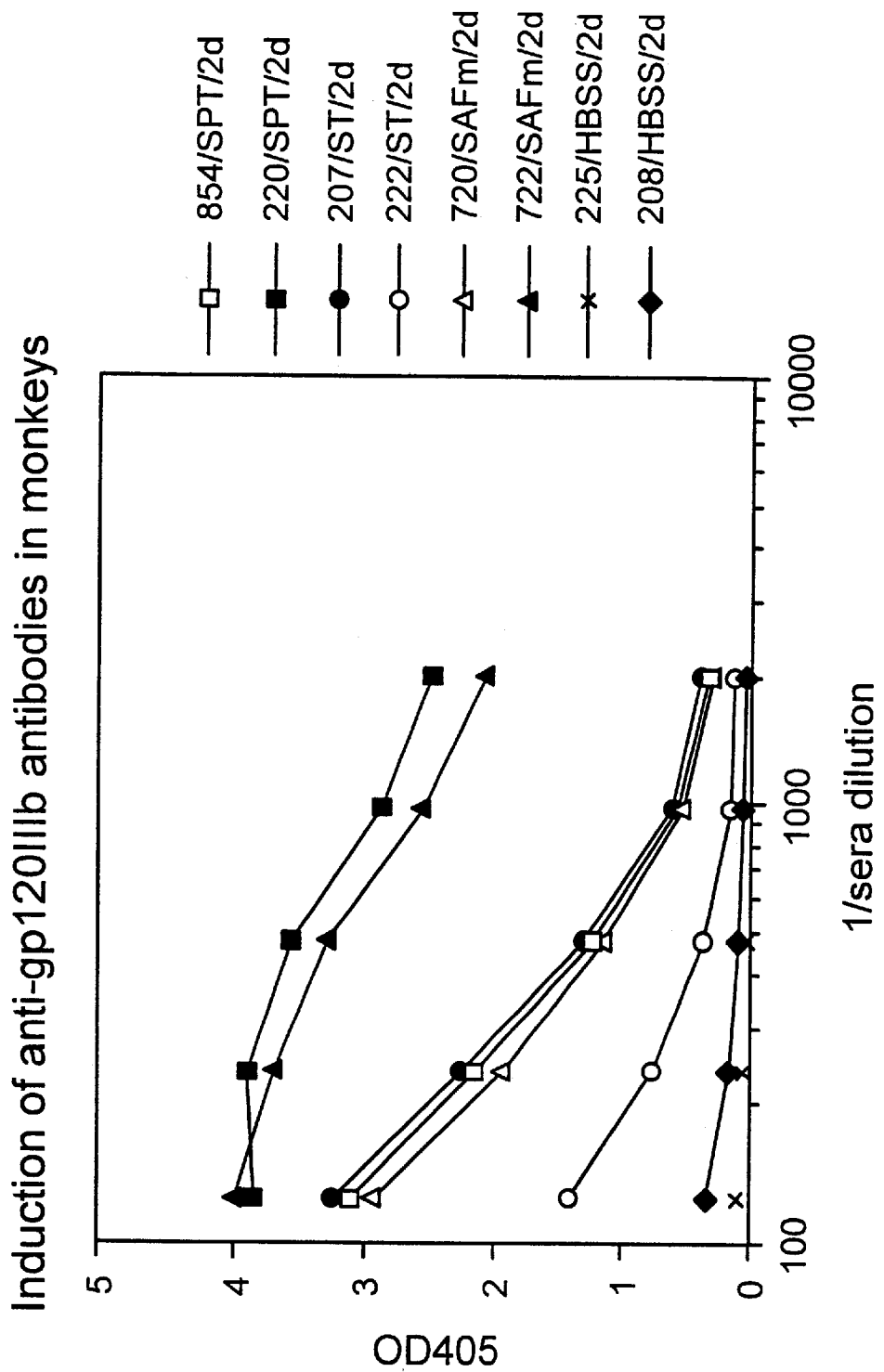
FIG. 12 is a graphical representation of the induction or anti-gp120IIIb antibodies with various antigen formulations.

Monkeys (two per group) were immunized with gp120-SAFm, gp120-SPT, gp120-ST, gp120-PT or gp120-HBSS. As a control, a group of monkeys were immunized with recombinant vaccinia containing gp160 IIIb. Monkeys were immunized at two week intervals and bled two weeks and three weeks after the second immunization. Pre and immune sera from each monkey was serially diluted and assayed for anti-gp120 activity in an ELISA as described in the materials and methods. The data (FIG. 12) indicate that monkeys immunized with gp120-STP or gp120-SAFm induced similar responses in monkeys. One monkey immunized with gp120-ST induced anti-gp120 response similar to gp120-SAFm or gp120-SPT immunized group. One monkey immunized with gp120-ST did not induce a strong anti-gp120 response after two immunizations.

Other embodiments are within the following claims.

said patient in an amount sufficient to induce a cytotoxic T-lymphocyte response in said patient.

2. The method of claim 1, wherein said HIV antigen is selected from gp160, gag, pol, Nef, Tat, and Rev.

3. A method of treating a human infected with malaria, comprising administering a composition comprising a malaria-associated antigen mixed with a microfluidized antigen formulation comprising:

(a) a stabilizing detergent,
(b) a micelle-forming agent, and
(c) a biodegradable and biocompatible oil, said antigen formulation lacking an immunostimulating peptide component, and being formulated as a stable oil-in-water emulsion; wherein said composition is administered to said patient in an amount sufficient to induce a cytotoxic T-lymphocyte response in said patient.

4. The method of claim 2, wherein said malaria-associated antigen is selected from CS protein, and Sporozoite surface protein 2.

---

---

We claim:

1. A method of treating a human infected with HIV virus, comprising administering a composition comprising an HIV antigen mixed with a microfluidized antigen formulation comprising:

(a) a stabilizing detergent,
(b) a micelle-forming agent, and
(c) a biodegradable and biocompatible oil, said antigen formulation lacking an immunostimulating peptide component, and being formulated as a stable oil-in-water emulsion; wherein said composition is administered to 5. A method of treating a human infected with influenza, comprising administering a composition comprising an influenza-associated antigen mixed with a microfluidized antigen formulation comprising:

(a) a stabilizing detergent,
(b) a micelle-forming agent, and
(c) a biodegradable and biocompatible oil, said antigen formulation lacking an immunostimulating peptide component, and being formulated as a stable oil-in-water emulsion; wherein said composition is administered to said patient in an amount sufficient to induce a cytotoxic T-lymphocyte response in said patient.

6. The method of claim 5, wherein said influenza-associated antigen is selected from HA, NP, and NA.

7. A method of treating a human infected with hepatitis, comprising administering a composition comprising a hepatitis-associated antigen mixed with a microfluidized formulation comprising:
   (a) a stabilizing detergent,
   (b) a micelle-forming agent, and
   (c) a biodegradable and biocompatible oil,
said antigen formulation lacking an immunostimulating peptide component, and being formulated as a stable oil-in-water emulsion; wherein said composition is administered to said patient in an amount sufficient to induce a cytotoxic T-lymphocyte response in said patient.

8. The method of claim 7, wherein said hepatitis-associated antigen is selected from hepatitis A surface antigen, Pre-S1, Pre-S2, HBc Ag, and HBe Ag.

9. A method of treating a human having a cancer, comprising administering a composition comprising a cancer-associated antigen mixed with a microfluidized antigen formulation comprising:
   (a) a stabilizing detergent,
   (b) a micelle-forming agent, and
   (c) a biodegradable and biocompatible oil,
said antigen formulation lacking an immunostimulating peptide component, and being formulated as a stable oil-in-water emulsion; wherein said composition is administered to said patient in an amount sufficient to induce a cytotoxic T-lymphocyte response in said patient.

10. A method of claim 9, wherein said cancer-associated antigen is selected from Carcinoma CEA, Carconoma associated mucin, P21, carcinoma P53, melanoma MPG, melanoma p97, and carcinoma Neu oncogene product, carcinoma p53 gene product, and mutated p21 ras protein.

11. A method of treating a human infected with herpes virus, comprising administering a composition comprising a herpes antigen mixed with a microfluidized antigen formulation comprising:
   (a) a stabilizing detergent,
   (b) a micelle-forming agent, and
   (c) a biodegradable and biocompatible oil,
said antigen formulation lacking an immunostimulating peptide component, and being formulated as a stable oil-in-water emulsion; wherein said composition is administered to said patient in an amount sufficient to induce a cytotoxic T-lymphocyte response in said patient.

12. The method of claim 11, wherein said herpes virus antigen is selected from EBV gp340, EBV gp85, HSV gB, HSV gD, HSV gH, HSV early protein product, cytomealovirus gB, cytomegalovirus gH and IE protein gP72.

13. A method of treating a human infected with respiratory syncytial virus, comprising administering a composition comprising a respiratory syncytial antigen mixed with a microfluidized antigen formulation comprising:
   (a) a stabilizing detergent,
   (b) a micelle-forming agent, and
   (c) a biodegradable and biocompatible oil,
said antigen formulation lacking an immunostimulating peptide component, and being formulated as a stable oil-in-water emulsion; wherein said composition is administered to said patient in an amount sufficient to induce a cytotoxic T-lymphocyte response in said patient.

14. The method of claim 13 wherein said Respiratory Syncytial virus antigen is selected from F protein, G protein, and N protein.

15. A method for inducing a cytotoxic T-lymphocyte response in a human, comprising the steps of:
administering a mixture of an antigen mixed with a microfluidized antigen formulation consisting essentially of two of:
   (a) a stabilizing detergent,
   (b) a micelle-forming agent, and
   (c) a biodegradable and biocompatible oil,
said antigen formulation being formulated as a stable oil-in-water emulsion;
wherein said mixture is administered to said human or animal in an amount sufficient to induce a cytotoxic T-lymphocyte response in said human or animal.

16. The method of claim 15, wherein said human is infected with a virus and suffers one or more symptoms of infection from said virus.

17. The method of claim 15, wherein said antigen formulation is non-toxic to said human.

18. The method or claim 15, wherein said antigen is chosen from antigenic portions of the HIV antigens: gp160, gag, pol, Nef, Tat, and Rev; the malaria antigens: CS protein and Sporczoite surface protein 2; the Hepatitis B surface antigens: Pre-S1, Pre-S2, HBc Ag, and HBe Ag; the influenza antigens: HA, NP and NA; Hepatitis A surface antigens; the Herpes virus antigens: EBV gp340, EBV gp85, HSV gB, HSV gD, HSV gH, HSV early protein product, cytomegalovirus gB, cytomegalovirus gH, and IE protein gP72; the respiratory syncytial virus antigens: F protein, G protein, and N protein; and the tumor antigens carcinoma CEA, carcinoma associated mucin, carcinoma P21, carcinoma P53, melanoma MPG, melanoma p97, and carcinoma Neu oncogene product, carcinoma p53 gene product, and mutated p21 ras protein.

19. A method of treating a human infected with HIV virus, comprising administering a composition comprising an HIV antigen mixed with a microfluidized antigen formulation consisting essentially of two of:
   (a) a stabilizing detergent,
   (b) a micelle-forming agent, and
   (c) a biodegradable and biocompatible oil,
said antigen formulation being formulated as a stable oil-in-water emulsion; wherein said composition is administered to said patient in an amount sufficient to induce a cytotoxic T-lymphocyte response in said patient.

20. The method of claim 19, wherein said HIV antigen is selected from gp160, gag, pol, Nef, Tat, and Rev.

21. A method of treating a human having malaria, comprising administering a composition comprising a malaria-associated antigen mixed with a microfluidized antigen formulation consisting essentially of two of:
   (a) stabilizing detergent,
   (b) a micelle-forming agent, and
   (c) a biodegradable and biocompatible oil,
said antigen formulation being formulated as a stable oil-in-water emulsion; wherein said composition is administered to said patient in an amount sufficient to induce a cytotoxic T-lymphocyte response in said patient.

22. The method of claim 21, wherein said malaria-associated antigen is selected from CS protein, and Sporozoite surface protein 2.

23. A method of treating a human infected with influenza, comprising administering a composition comprising an influenza-associated antigen mixed with a microfluidized antigen formulation consisting essentially of two of:
   (a) a stabilizing detergent,
   (b) a micelle-forming agent, and
   (c) a biodegradable and biocompatible oil,
said antigen formulation being formulated as a stable oil-in-water emulsion; wherein said composition is administered to said patient in an amount sufficient to induce a cytotoxic T-lymphocyte response in said patient.

24. The method of claim 23, wherein said influenza-associated antigen is selected from HA, NP, and NA.

25. A method of treating a human having hepatitis, comprising administering a composition comprising a hepatitis-associated antigen mixed with a microfluidized antigen formulation consisting essentially of two of:
   (a) a stabilizing detergent,
   (b) a micelle-forming agent, and
   (c) a biodegradable and biocompatible oil,
said antigen formulation being formulated as a stable oil-in-water emulsion; wherein said composition is administered to said patient in an amount sufficient to induce a cytotoxic T-lymphocyte response in said patient.

26. The method of claim 25, wherein said hepatitis-associated antigen is selected from hepatitis A surface antigen, Pre-S1, Pre-S2, HBc Ag, and HBe Ag.

27. A method of treating a human having a cancer, comprising administering a composition comprising a cancer-associated antigen mixed with a microfluidized antigen formulation consisting essentially of two of:
   (a) a stabilizing detergent,
   (b) a micelle-forming agent, and
   (c) a biodegradable and biocompatible oil,
said antigen formulation being formulated as a stable oil-in-water emulsion; wherein said composition is administered to said patient in an amount sufficient to induce a cytotoxic T-lymphocyte response in said patient.

28. The method of claim 27, wherein said cancer-associated antigen is selected from Carcinoma CEA, Carconoma associated mucin, P21, carcinoma P53, melanoma MPG, melanoma p97, and carcinoma Neu oncogene product, carcinoma p53 gene product, and mutated p21 ras protein.

29. A method of treating a human infected with herpes virus, comprising administering a composition comprising a herpes antigen mixed with a microfluidized antigen formulation consisting essentially of two of:
   (a) stabilizing detergent,
   (b) a micelle-forming agent, and
   (c) a biodegradable and biocompatible oil,
said antigen formulation being formulated as a stable oil-in-water emulsion; wherein said composition is administered to said patient in an amount sufficient to induce a cytotoxic T-lymphocyte response in said patient.

30. The method of claim 29, wherein said herpes virus antigen is selected from EBV gp340, EBV gp85, HSV gB, HSV gD, HSV gH, HSV early protein product, cytomegalovirus gB, cytomegalovirus gH and IE protein gP72.

31. A method of treating a human infected with respiratory syncytial virus, comprising administering a respiratory syncytial antigen mixed with a microfluidized antigen formulation consisting essentially of two of:
   (a) stabilizing detergent,
   (b) a micelle-forming agent, and
   (c) a biodegradable and biocompatible oil,
said antigen formulation being formulated as a stable oil-in-water emulsion; wherein said composition is administered to said patient in an amount sufficient to induce a cytotoxic T-lymphocyte response in said patient.

32. The method of claim 31 wherein said Respiratory Syncytial virus antigen is selected from F protein, G protein, and N protein.

33. The method of any of claims 13–32 wherein said antigen formulation consists essentially of said detergent and said micelle-forming agent.

34. The method of any of claims 13–32 wherein said antigen formulation consists essentially of said detergent and said oil.

35. The method of any of claims 13–32 wherein said antigen formulation consists essentially of said oil and said micelle-forming agent.

* * * * *